(12) United States Patent
Miyake et al.

(10) Patent No.: US 11,420,919 B2
(45) Date of Patent: Aug. 23, 2022

(54) PROCESS FOR PREPARING A FORMYLALKENYL ALKOXYMETHYL ETHER COMPOUND AND PROCESSES FOR PREPARING CONJUGATED DIENE COMPOUNDS FROM THE SAME

(71) Applicant: Shin-Etsu Chemical Co., Ltd., Tokyo (JP)

(72) Inventors: Yuki Miyake, Niigata (JP); Takeshi Kinsho, Niigata (JP); Miyoshi Yamashita, Niigata (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 9 days.

(21) Appl. No.: 17/209,979

(22) Filed: Mar. 23, 2021

(65) Prior Publication Data
US 2021/0300854 A1    Sep. 30, 2021

(30) Foreign Application Priority Data

Mar. 27, 2020    (JP) .............................. JP2020-059025

(51) Int. Cl.
| | | |
|---|---|---|
| *C07C 45/42* | (2006.01) | |
| *C07C 29/10* | (2006.01) | |
| *C07C 67/24* | (2006.01) | |
| *C07C 33/02* | (2006.01) | |
| *C07C 49/255* | (2006.01) | |
| *C07C 69/587* | (2006.01) | |

(52) U.S. Cl.
CPC .............. *C07C 45/42* (2013.01); *C07C 29/10* (2013.01); *C07C 67/24* (2013.01); *C07C 33/02* (2013.01); *C07C 49/255* (2013.01); *C07C 69/587* (2013.01)

(58) Field of Classification Search
CPC ......... C07C 45/42; C07C 29/10; C07C 67/24; C07C 33/02; C07C 69/587
See application file for complete search history.

(56) References Cited

U.S. PATENT DOCUMENTS

2009/0143617 A1*  6/2009  Yamashita .............. C07C 41/50
562/598

FOREIGN PATENT DOCUMENTS

JP    2009132647 A    6/2009

OTHER PUBLICATIONS

Ando et al. "Sex Pheromones of Thysanoplusia intermixta and T. orichalcea: Identification and Field Tests" Journal of Chemical Ecology, 24(6):1105-1116 (1998).
Wu et al. "Enantioselective Cascade Sequence to Indoloquinolizidines and Its Application in the Synthesis of epi-Geissochizol" Synthesis, 22:3675-3679 (2011).

* cited by examiner

*Primary Examiner* — Yate' K Cutliff
(74) *Attorney, Agent, or Firm* — Myers Bigel, P.A.

(57) ABSTRACT

The present invention provide for preparing a formylalkenyl alkoxymethyl ether compound of the following general formula (2): $R^3CH_2OCH_2O(CH_2)_aCH=CHCHO$ (2), wherein $R^3$ represents a hydrogen atom, an n-alkyl group having 1 to 9 carbon atoms, or a phenyl group; and "a" represents an integer of 1 to 10, the process comprising: hydrolyzing a dialkoxyalkenyl alkoxymethyl ether compound of the following general formula (1): $R^3CH_2OCH_2O(CH_2)_aCH=CHCH(OR^1)(OR^2)$ (1), wherein $R^1$ and $R^2$ represent, independently of each other, a monovalent hydrocarbon group having 1 to 15 carbon atoms, or $R^1$ and $R^2$ may form together a divalent hydrocarbon group, $R^1$-$R^2$, having 2 to 10 carbon atoms; and $R^3$ and "a" are as defined above, in the presence of an acid while removing an alcohol compound thus generated to form the formylalkenyl alkoxymethyl ether compound (2).

6 Claims, No Drawings

PROCESS FOR PREPARING A FORMYLALKENYL ALKOXYMETHYL ETHER COMPOUND AND PROCESSES FOR PREPARING CONJUGATED DIENE COMPOUNDS FROM THE SAME

CROSS-REFERENCE TO RELATED APPLICATION

This U.S. nonprovisional application claims priority to Japanese Application No. 2020-059025 filed Mar. 27, 2020, the entire contents of which are incorporated herein by reference.

TECHNICAL FIELD

The present invention relates to a process for preparing a formylalkenyl alkoxymethyl ether compound and processes for preparing conjugated diene compounds from the same.

BACKGROUND ART

Formylalkenyl alkoxymethyl ether compounds are useful to construct a conjugated diene backbone via a Wittig reaction and, therefore, very useful as a precursor for synthesizing an insect pheromone having a conjugated diene backbone. Examples of the insect pheromone having a conjugated diene backbone include (5E,7Z)-5,7-dodecadiene-1-ol and (5E,7Z)-5,7-dodecadienyl acetate which are sex pheromones of *Thysanoplusia intermixta* (Non-Patent Literature 1 listed below).

Reported processes for synthesizing formylalkenyl alkoxymethyl ether compounds include a process comprising subjecting (Z)-5,5-diethoxy-3-pentenyl methoxymethyl ether to a hydrolysis with hydrochloric acid, followed by extraction with toluene (Patent Literature 1 listed below) and a process comprising subjecting 5-(methoxymethoxy)-2-pentyne-1-ol to hydroalumination with lithium aluminum hydride, followed by Parikh-Doering oxidation (Non-Patent Literature 2 listed below).

LIST OF THE PRIOR LITERATURES

[Patent Literature 1] Japanese Patent Application Laid-Open No. 2009-132647
[Non-Patent Literature 1] T. Ando, J. Chem. Ecol., 1998, 24 (6), 1105-1116.
[Non-Patent Literature 2] Xiaoyu Wu et al., Synthesis, 2011, 22, 3675-3679.

Problems to be Solved by the Invention

However, the process described in Non-Patent Literature 2 uses lithium aluminum hydride, which is may catch fire and, therefore, this process is improper for industrial application. The aforesaid Parikh-Doering oxidation uses dimethyl sulfoxide to by-produce bad-smelling dimethyl sulfide in the reaction. Dimethyl sulfide of a high concentration may cause oxygen-deficient air, resulting, at worst, death. Dimethyl sulfide may react with an oxidizing agent to cause accidents such as a fire or an explosion. Further, a mixture gas of dimethyl sulfide, which is a specified inflammable material, with air is explosive and thus requires a special therefore, the production facility or treatment facility. Therefore, the process described in Non-Patent Literature 2 is not proper for industrial application. In addition, dichloromethane is used as a solvent in the process. Dichloromethane causes an extremely high environmental load, which is unfavorable in view of environmental conservation.

Meanwhile, in the process described in Patent Literature 1, the hydrolysis is an equilibrium reaction. Therefore, a certain amount of the raw material, (Z)-5,5-diethoxy-3-pentenyl methoxymethyl ether, remains unreacted, so that the reaction is not completed and it is necessary to monitor the progress of the reaction, while sampling a reaction mixture. In the process described in Patent Literature 1, it is necessary to selectively hydrolyze a diethylacetal part which is a protecting group for the carbonyl group, not the methoxymethyl (MOM) group which is a protecting group for the hydroxyl group. However, ethanol formed in the hydrolysis of the methoxymethyl group and hydrochloric acid used in the hydrolysis cause release of the protecting methoxymethyl group. Therefore, a yield is not stable. Further, the formed ethanol causes 1,4-addition to the target compound, (E)-4-formyl-3-butenyl methoxymethyl ether to form a by-product, (E)-4-formyl-3-ethoxybutyl methoxymethyl ether, resulting in a low purity. Thus, it is not easy to selectively hydrolyze the dialkylacetal part only among the dialkylacetal part and the alkoxy methyl group present in one and the same molecule. Therefore, there is a demand for a process for selectively hydrolyzing the dialkylacetal part in the hydrolysis of a dialkoxyalkenyl alkoxymethyl ether compound to prepare a formylalkenyl alkoxymethyl ether compound at a high yield.

SUMMARY OF THE INVENTION

A purpose of the present invention is to overcome the aforesaid problems and prepare a formylalkenyl alkoxymethyl ether compound in a high purity and a high yield by suppressing removable of an alkoxymethyl group of the dialkoxyalkenyl alkoxymethyl ether compound and selectively hydrolyzing an acetal part only. Another purpose of the present invention is to provide a process for preparing a formylalkenyl alkoxymethyl ether compound, which process is preferred in view of environmental conservation and productivity.

As a result of the intensive researches, the present inventors have found that formylalkenyl alkoxymethyl ether compounds is stably prepared in a high yield and high purity, without using extraction solvent and/or sampling a reaction mixture during the reaction, by carrying out a hydrolysis in the presence of an acid and proceeding with the hydrolysis, while removing an alcohol compound formed by the hydrolysis, and thus have completed the present invention. The present inventors have also found a process for preparing (5E,7Z)-5,7-dodecadiene-1-ol and (5E,7Z)-5,7-dodecadienyl acetate in a high yield from formylalkenyl alkoxymethyl ether compound, and thus have completed the present invention.

In an aspect of the present invention, there is provided a process for preparing a formylalkenyl alkoxymethyl ether compound of the following general formula (2):

$$R^3CH_2OCH_2O(CH_2)_aCH\!=\!\!CHCHO \qquad (2)$$

wherein $R^3$ represents a hydrogen atom, an n-alkyl group having 1 to 9 carbon atoms, or a phenyl group; and "a" represents an integer of 1 to 10, the process comprising hydrolyzing a dialkoxyalkenyl alkoxymethyl ether compound of the following general formula (1):

$$R^3CH_2OCH_2O(CH_2)_aCH=CHCH(OR^1)(OR^2) \quad (1)$$

wherein $R^1$ and $R^2$ represent, independently of each other, a monovalent hydrocarbon group having 1 to 15 carbon atoms, or $R^1$ and $R^2$ may form together a divalent hydrocarbon group, $R^1$-$R^2$, having 2 to 10 carbon atoms; and $R^3$ and "a" are as defined above,
in the presence of an acid while removing an alcohol compound thus generated to form the formylalkenyl alkoxymethyl ether compound (2).

In another aspect of the present invention, there is provided a process for preparing a (5E,7Z)-5,7-dodecadiene-1-ol of the following formula (5):

$$CH_3(CH_2)_3CH=CHCH=CH(CH_2)_4OH \quad (5)$$

the process comprising the aforesaid process for preparing the formylalkenyl alkoxymethyl ether compound (2), provided that "a" is 4, subjecting the formylalkenyl alkoxymethyl ether compound (2) thus obtained, and a triarylphosphonium pentylide compound of the following general formula (3):

$$Ar_3\overset{\oplus}{P}\overset{\ominus}{C}H(CH_2)_3CH_3 \quad (3)$$

wherein Ar represents, independently of each other, an aryl group,
to a Wittig reaction to form a (5E,7Z)-5,7-dodecadienyl alkoxymethyl ether compound of the following general formula (4):

$$CH_3(CH_2)_3CH=CHCH=CH(CH_2)_4OCH_2OCH_2R^3 \quad (4)$$

wherein $R^3$ is as defined above; and
subjecting the (5E,7Z)-5,7-dodecadienyl alkoxymethyl ether compound (4) to dealkoxymethylation to form the (5E,7Z)-5,7-dodecadiene-1-ol (5).

In a further another aspect of the present invention, there is provided a process for preparing a (5E,7Z)-5,7-dodecadienyl acetate of the following formula (6):

$$CH_3(CH_2)_3CH=CHCH=CH(CH_2)_4OCOCH_3 \quad (6)$$

the process comprising:

the aforesaid process for preparing the (5E,7Z)-5,7-dodecadiene-1-ol (5), and subjecting the (5E,7Z)-5,7-dodecadiene-1-ol (5) thus obtained to an acetylation to form the (5E,7Z)-5,7-dodecadienyl acetate (6).

According to the present invention, the progress of the hydrolysis can be monitored by measuring a weight of weighing the alcohol compound which is removed during the reaction. This eliminates necessity of sampling a reaction mixture for monitoring the progress of the reaction and also improve workability and safety. According to the present process, an amount of alcohol present in the reaction system during the reaction is smaller. Accordingly, by-production of (E)-4-formyl-3-alkoxybutyl alkoxymethyl ether is suppressed and, further, the reaction is more completed, without leaving the dialkoxyalkenyl alkoxymethyl ether compound unreacted. Thus, the formylalkenyl alkoxymethyl ether compound (2) may be prepared less expensively in high productivity, a high yield and a high purity. Further, according to the present invention, (5E,7Z)-5,7-dodecadiene-1-ol (5) and (5E,7Z)-5,7-dodecadienyl acetate (6), which are sex pheromones of *Thysanoplusia intermixta*, may be prepared in a high yield, starting from the thus produced formylalkenyl alkoxymethyl ether compound (2).

DETAILED DESCRIPTION OF THE PREFERRED EMBODIMENTS

A formylalkenyl alkoxymethyl ether compound of the following general formula (2) (hereinafter referred to also as formylalkenyl alkoxymethyl ether compound (2)) is obtained by subjecting a dialkoxyalkenyl alkoxymethyl ether compound of the following general formula (1) (hereinafter referred to also as dialkoxyalkenyl alkoxymethyl ether compound (1)) to hydrolysis in the presence of an acid.

$$R^3CH_2OCH_2O(CH_2)_aCH=CHCH(OR^1)(OR^2) \quad (1)$$

$$R^3CH_2OCH_2O(CH_2)_aCH=CHCHO \quad (2)$$

The dialkoxyalkenyl alkoxymethyl ether compound (1) will be first explained hereinafter.

In the general formula (1), $R^1$ and $R^2$ represent, independently of each other, a monovalent hydrocarbon group having 1 to 15, preferably 1 to 4 carbon atoms, or $R^1$ and $R^2$ may be form together a divalent hydrocarbon group, $R^1$-$R^2$, having 2 to 10 carbon atoms, preferably 2 to 5 carbon atoms, and more preferably 2 to 4 carbon atoms.

Examples of the monovalent hydrocarbon group for $R^1$ and $R^2$ include linear saturated hydrocarbon groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, and an n-pentadecyl group; branched saturated hydrocarbon groups such as an isopropyl group, a 2-methyl butyl group, and a t-butyl group; branched unsaturated hydrocarbon groups such as a 2-methyl-2-propenyl group; cyclic saturated hydrocarbon groups such as a cyclopropyl group; aryl groups such as a phenyl group; and isomers thereof. A part of the hydrogen atoms in the hydrocarbon groups may be substituted with a methyl group or an ethyl group.

Examples of the divalent hydrocarbon group for $R^1$-$R^2$ include linear saturated hydrocarbon groups such as an ethylene group, a 1,3-propylene group, a 1,4-butylene group, a 1,5-pentylene group, a 1,6-hexylene group, a 1,7-heptylene group, a 1,8-octylene group, a 1,9-nonylene group, a 1,10-decylene group, a 1,11-undecylene group, a 1,12-dodecylene group, a 1,13-tridecylene group, a 1,14-tetradecylene group, and a 1,15-pentadecylene; linear unsaturated hydrocarbon groups such as a 1-vinylethylene group; branched saturated hydrocarbon groups such as a 1,2-propylene group, a 2,2-dimethyl-1,3-propylene group, a 1,2-butylene group, a 1,3-butylene group, a 2,3-butylene group, and a 2,3-dimethyl-2,3-butylene group; branched unsaturated hydrocarbon groups such as a 2-methylene-1,3-propylene group; cyclic hydrocarbon groups such as a 1,2-cyclopropylene group and a 1,2-cyclobutylene group; and isomers thereof. A part of the hydrogen atoms in the hydrocarbon groups may be substituted with a methyl group or an ethyl group.

The divalent hydrocarbon group is preferably a highly reactive, lower hydrocarbon group (preferably having 2 to 4 carbon atoms), because such is easily available, shows favorable reactivity in deprotection, and forms a by-product easily removable by washing or evaporation so as to make purification easier.

In this sense, preferred examples of the divalent hydrocarbon group include an ethylene group, a 1,2-propylene group, a 1,3-propylene group, a 1,2-butylene group, a 1,3-butylene group, and a 2,3-dimethyl-2,3-butylene group.

In the general formula (1), "a" represents an integer of 1 to 10, preferably 1 to 4.

In the general formula (1), $R^3$ represents a hydrogen atom, an n-alkyl group having 1 to 9 carbon atoms, preferably 1 to 4, carbon atoms, or a phenyl group.

Specific examples of the dialkoxyalkenyl alkoxymethyl ether compound (1) include dialkoxybutenyl alkoxymethyl ether compounds such as dimethoxybutenyl methoxymethyl ether, diethoxybutenyl methoxymethyl ether, dipropoxybutenyl methoxymethyl ether, dibutoxybutenyl methoxymethyl ether, dipentyloxybutenyl methoxymethyl ether, dihexyloxybutenyl methoxymethyl ether, diheptyloxybutenyl methoxymethyl ether, dioctyloxybutenyl methoxymethyl ether, dinonyloxybutenyl methoxymethyl ether, and didecyloxybutenyl methoxymethyl ether; dialkoxypentenyl methoxymethyl ether compounds such as dimethoxypentenyl methoxymethyl ether, diethoxypentenyl methoxymethyl ether, dipropoxypentenyl methoxymethyl ether, dibutoxypentenyl methoxymethyl ether, dipentyloxypentenyl methoxymethyl ether, dihexyloxypentenyl methoxymethyl ether, diheptyloxypentenyl methoxymethyl ether, dioctyloxypentenyl methoxymethyl ether, dinonyloxypentenyl methoxymethyl ether, and didecyloxypentenyl methoxymethyl ether; dialkoxypentenyl ethoxymethyl ether compounds such as dimethoxypentenyl ethoxymethyl ether, diethoxypentenyl ethoxymethyl ether, dipropoxypentenyl ethoxymethyl ether, dibutoxypentenyl ethoxymethyl ether, dipentyloxypentenyl ethoxymethyl ether, dihexyloxypentenyl ethoxymethyl ether, diheptyloxypentenyl ethoxymethyl ether, dioctyloxypentenyl ethoxymethyl ether, dinonyloxypentenyl ethoxymethyl ether, and didecyloxypentenyl ethoxymethyl ether; dialkoxypentenyl propoxymethyl ether compounds such as dimethoxypentenyl propoxymethyl ether, diethoxypentenyl propoxymethyl ether, dipropoxypentenyl propoxymethyl ether, dibutoxypentenyl propoxymethyl ether, dipentyloxypentenyl propoxymethyl ether, dihexyloxypentenyl propoxymethyl ether, diheptyloxypentenyl propoxymethyl ether, dioctyloxypentenyl propoxymethyl ether, dinonyloxypentenyl propoxymethyl ether, and didecyloxypentenyl propoxymethyl ether; dialkoxypentenyl butoxymethyl ether compounds such as dimethoxypentenyl butoxymethyl ether, diethoxypentenyl butoxymethyl ether, dipropoxypentenyl butoxymethyl ether, dibutoxypentenyl butoxymethyl ether, dipentyloxypentenyl butoxymethyl ether, dihexyloxypentenyl butoxymethyl ether, diheptyloxypentenyl butoxymethyl ether, dioctyloxypentenyl butoxymethyl ether, dinonyloxypentenyl butoxymethyl ether, and didecyloxypentenyl butoxymethyl ether; dialkoxypentenyl pentyloxymethyl ether compounds such as dimethoxypentenyl pentyloxymethyl ether, diethoxypentenyl pentyloxymethyl ether, dipropoxypentenyl pentyloxymethyl ether, dibutoxypentenyl pentyloxymethyl ether, dipentyloxypentenyl pentyloxymethyl ether, dihexyloxypentenyl pentyloxymethyl ether, diheptyloxypentenyl pentyloxymethyl ether, dioctyloxypentenyl pentyloxymethyl ether, dinonyloxypentenyl pentyloxymethyl ether, and didecyloxypentenyl pentyloxymethyl ether; dialkoxypentenyl hexyloxymethyl ether compounds such as dimethoxypentenyl hexyloxymethyl ether, diethoxypentenyl hexyloxymethyl ether, dipropoxypentenyl hexyloxymethyl ether, dibutoxypentenyl hexyloxymethyl ether, dipentyloxypentenyl hexyloxymethyl ether, dihexyloxypentenyl hexyloxymethyl ether, diheptyloxypentenyl hexyloxymethyl ether, dioctyloxypentenyl hexyloxymethyl ether, dinonyloxypentenyl hexyloxymethyl ether, and didecyloxypentenyl hexyloxymethyl ether; dialkoxypentenyl heptyloxymethyl ether compounds such as dimethoxypentenyl heptyloxymethyl ether, diethoxypentenyl heptyloxymethyl ether, dipropoxypentenyl heptyloxymethyl ether, dibutoxypentenyl heptyloxymethyl ether, dipentyloxypentenyl heptyloxymethyl ether, dihexyloxypentenyl heptyloxymethyl ether, diheptyloxypentenyl heptyloxymethyl ether, dioctyloxypentenyl heptyloxymethyl ether, dinonyloxypentenyl heptyloxymethyl ether, and didecyloxypentenyl heptyloxymethyl ether; dialkoxypentenyl octyloxymethyl ether compounds such as dimethoxypentenyl octyloxymethyl ether, diethoxypentenyl octyloxymethyl ether, dipropoxypentenyl octyloxymethyl ether, dibutoxypentenyl octyloxymethyl ether, dipentyloxypentenyl octyloxymethyl ether, dihexyloxypentenyl octyloxymethyl ether, diheptyloxypentenyl octyloxymethyl ether, dioctyloxypentenyl octyloxymethyl ether, dinonyloxypentenyl octyloxymethyl ether, and didecyloxypentenyl octyloxymethyl ether; dialkoxypentenyl nonyloxymethyl ether compounds such as dimethoxypentenyl nonyloxymethyl ether, diethoxypentenyl nonyloxymethyl ether, dipropoxypentenyl nonyloxymethyl ether, dibutoxypentenyl nonyloxymethyl ether, dipentyloxypentenyl nonyloxymethyl ether, dihexyloxypentenyl nonyloxymethyl ether, diheptyloxypentenyl nonyloxymethyl ether, dioctyloxypentenyl nonyloxymethyl ether, dinonyloxypentenyl nonyloxymethyl ether, and didecyloxypentenyl nonyloxymethyl ether; dialkoxypentenyl decyloxymethyl ether compounds such as dimethoxypentenyl decyloxymethyl ether, diethoxypentenyl decyloxymethyl ether, dipropoxypentenyl decyloxymethyl ether, dibutoxypentenyl decyloxymethyl ether, dipentyloxypentenyl decyloxymethyl ether, dihexyloxypentenyl decyloxymethyl ether, diheptyloxypentenyl decyloxymethyl ether, dioctyloxypentenyl decyloxymethyl ether, dinonyloxypentenyl decyloxymethyl ether, and didecyloxypentenyl decyloxymethyl ether; dialkoxypentenyl benzyloxymethyl ether compounds such as dimethoxypentenyl benzyloxymethyl ether, diethoxypentenyl benzyloxymethyl ether, dipropoxypentenyl benzyloxymethyl ether, dibutoxypentenyl benzyloxymethyl ether, dipentyloxypentenyl benzyloxymethyl ether, dihexyloxypentenyl benzyloxymethyl ether, diheptyloxypentenyl benzyloxymethyl ether, dioctyloxypentenyl benzyloxymethyl ether, dinonyloxypentenyl benzyloxymethyl ether, and didecyloxypentenyl benzyloxymethyl ether; dialkoxyhexenyl alkoxymethyl ether compounds such as dimethoxyhexenyl methoxymethyl ether, diethoxyhexenyl methoxymethyl ether, dipropoxyhexenyl methoxymethyl ether, dibutoxyhexenyl methoxymethyl ether, dipentyloxyhexenyl methoxymethyl ether, dihexyloxyhexenyl methoxymethyl ether, diheptyloxyhexenyl methoxymethyl ether, dioctyloxyhexenyl methoxymethyl ether, dinonyloxyhexenyl methoxymethyl ether, and didecyloxyhexenyl methoxymethyl ether; dialkoxyheptenyl methoxymethyl ether compounds such as dimethoxyheptenyl methoxymethyl ether, diethoxyheptenyl methoxymethyl ether, dipropoxyheptenyl methoxymethyl ether, dibutoxyheptenyl methoxymethyl ether, dipentyloxyheptenyl methoxymethyl ether, dihexyloxyheptenyl methoxymethyl ether, diheptyloxyheptenyl methoxymethyl ether, dioctyloxyheptenyl methoxymethyl ether, dinonyloxyheptenyl methoxymethyl ether, and didecyloxyheptenyl methoxymethyl ether; dialkoxyheptenyl ethoxymethyl ether compounds such as dimethoxyheptenyl ethoxymethyl ether, diethoxyheptenyl ethoxymethyl ether, dipropoxyheptenyl ethoxymethyl ether, dibutoxyheptenyl ethoxymethyl ether, dipentyloxyheptenyl ethoxymethyl ether, dihexyloxyheptenyl ethoxymethyl ether, diheptyloxyheptenyl ethoxymethyl ether, dioctyloxyheptenyl ethoxymethyl ether, dinonyloxyheptenyl ethoxymethyl ether, and didecyloxyheptenyl ethoxymethyl ether; dialkoxyheptenyl propoxymethyl ether compounds such as dimethoxyheptenyl propoxymethyl ether, diethoxyheptenyl propoxymethyl ether, dipropoxyheptenyl propoxymethyl ether, dibutoxyheptenyl propoxymethyl ether, dipentyloxyheptenyl propoxymethyl ether, dihexyloxyheptenyl propoxymethyl ether, diheptyloxyheptenyl propoxymethyl ether, dioctyloxyheptenyl propoxymethyl ether, dinonyloxyheptenyl propoxymethyl ether, and didecyloxyheptenyl propoxymethyl ether; dialkoxyheptenyl butoxymethyl ether compounds such as dimethoxyheptenyl butoxymethyl ether, diethoxyheptenyl butoxymethyl ether, dipropoxyheptenyl butoxymethyl ether, dibutoxyheptenyl butoxymethyl ether, dipentyloxyheptenyl butoxymethyl ether, dihexyloxyheptenyl butoxymethyl ether, diheptyloxyheptenyl butoxymethyl ether, dioctyloxyheptenyl butoxymethyl ether, dinonyloxyheptenyl butoxymethyl ether, and didecyloxyheptenyl butoxymethyl ether; dialkoxyheptenyl pentyloxymethyl ether compounds such as dimethoxyheptenyl pentyloxymethyl ether, diethoxyheptenyl pentyloxymethyl ether, dipropoxyheptenyl pentyloxymethyl ether, dibutoxyheptenyl pentyloxymethyl ether, dipentyloxyheptenyl pentyloxymethyl ether, dihexyloxyheptenyl pentyloxymethyl ether, diheptyloxyheptenyl pentyloxymethyl ether, dioctyloxyheptenyl pentyloxymethyl ether, dinonyloxyheptenyl pentyloxymethyl ether, and didecyloxyheptenyl pentyloxymethyl ether; dialkoxyheptenyl hexyloxymethyl ether compounds such as dimethoxyheptenyl hexyloxymethyl ether, diethoxyheptenyl hexyloxymethyl ether, dipropoxyheptenyl hexyloxymethyl ether, dibutoxyheptenyl hexyloxymethyl ether, dipentyloxyheptenyl hexyloxymethyl ether, dihexyloxyheptenyl hexyloxymethyl ether, diheptyloxyheptenyl hexyloxymethyl ether, dioctyloxyheptenyl hexyloxymethyl ether, a dinonyloxyheptenyl hexyloxymethyl ether compound, and didecyloxyheptenyl hexyloxymethyl ether; dialkoxyheptenyl heptyloxymethyl ether compounds such as dimethoxyheptenyl heptyloxymethyl ether, diethoxyheptenyl heptyloxymethyl ether, dipropoxyheptenyl heptyloxymethyl ether, dibutoxyheptenyl heptyloxymethyl ether, dipentyloxyheptenyl heptyloxymethyl ether, dihexyloxyheptenyl heptyloxymethyl ether, diheptyloxyheptenyl heptyloxymethyl ether, dioctyloxyheptenyl heptyloxymethyl ether, dinonyloxyheptenyl heptyloxymethyl ether, and didecyloxyheptenyl heptyloxymethyl ether; dialkoxyheptenyl octyloxymethyl ether compounds such as dimethoxyheptenyl octyloxymethyl ether, diethoxyheptenyl octyloxymethyl ether, dipropoxyheptenyl octyloxymethyl ether, dibutoxyheptenyl octyloxymethyl ether, dipentyloxyheptenyl octyloxymethyl ether, dihexyloxyheptenyl octyloxymethyl ether, diheptyloxyheptenyl octyloxymethyl ether, dioctyloxyheptenyl octyloxymethyl ether, dinonyloxyheptenyl octyloxymethyl ether, and didecyloxyheptenyl octyloxymethyl ether; dialkoxyheptenyl nonyloxymethyl ether compounds such as dimethoxyheptenyl nonyloxymethyl ether, diethoxyheptenyl nonyloxymethyl ether, dipropoxyheptenyl nonyloxymethyl ether, dibutoxyheptenyl nonyloxymethyl ether, dipentyloxyheptenyl nonyloxymethyl ether, dihexyloxyheptenyl nonyloxymethyl ether, diheptyloxyheptenyl nonyloxymethyl ether, dioctyloxyheptenyl nonyloxymethyl ether, dinonyloxyheptenyl nonyloxymethyl ether, and didecyloxyheptenyl nonyloxymethyl ether; dialkoxyheptenyl decyloxymethyl ether compounds such as dimethoxyheptenyl decyloxymethyl ether, diethoxyheptenyl decyloxymethyl ether, dipropoxyheptenyl decyloxymethyl ether, dibutoxyheptenyl decyloxymethyl ether, dipentyloxyheptenyl decyloxymethyl ether, dihexyloxyheptenyl decyloxymethyl ether, diheptyloxyheptenyl decyloxymethyl ether, dioctyloxyheptenyl decyloxymethyl ether, dinonyloxyheptenyl decyloxymethyl ether, and didecyloxyheptenyl decyloxymethyl ether; dialkoxyheptenyl benzyloxymethyl ether compounds such as dimethoxyheptenyl benzyloxymethyl ether, diethoxyheptenyl benzyloxymethyl ether, dipropoxyheptenyl benzyloxymethyl ether, dibutoxyheptenyl benzyloxymethyl ether, dipentyloxyheptenyl benzyloxymethyl ether, dihexyloxyheptenyl benzyloxymethyl ether, diheptyloxyheptenyl benzyloxymethyl ether, dioctyloxyheptenyl benzyloxymethyl ether, dinonyloxyheptenyl benzyloxymethyl ether, and didecyloxyheptenyl benzyloxymethyl ether; dialkoxyoctenyl alkoxymethyl ether compounds such as dimethoxyoctenyl methoxymethyl ether, diethoxyoctenyl methoxymethyl ether, dipropoxyoctenyl methoxymethyl ether, dibutoxyoctenyl methoxymethyl ether, dipentyloxyoctenyl methoxymethyl ether, dihexyloxyoctenyl methoxymethyl ether, diheptyloxyoctenyl methoxymethyl ether, dioctyloxyoctenyl methoxymethyl ether, dinonyloxyoctenyl methoxymethyl ether, and didecyloxyoctenyl methoxymethyl ether; dialkoxynonenyl alkoxymethyl ether compounds such as dimethoxynonenyl methoxymethyl ether, diethoxynonenyl methoxymethyl ether, dipropoxynonenyl methoxymethyl ether, dibutoxynonenyl methoxymethyl ether, dipentyloxynonenyl methoxymethyl ether, dihexyloxynonenyl methoxymethyl ether, diheptyloxynonenyl methoxymethyl ether, dioctyloxynonenyl methoxymethyl ether, dinonyloxynonenyl methoxymethyl ether, and didecyloxynonenyl methoxymethyl ether; dialkoxydecenyl alkoxymethyl ether compounds such as dimethoxydecenyl methoxymethyl ether, diethoxydecenyl methoxymethyl ether, dipropoxydecenyl methoxymethyl ether, dibutoxydecenyl methoxymethyl ether, dipentyloxydecenyl methoxymethyl ether, dihexyloxydecenyl methoxymethyl ether, diheptyloxydecenyl methoxymethyl ether, dioctyloxydecenyl methoxymethyl ether, dinonyloxydecenyl methoxymethyl ether, and didecyloxydecenyl methoxymethyl ether; dialkoxyundecenyl alkoxymethyl ether compounds such as dimethoxyundecenyl methoxymethyl ether, diethoxyundecenyl methoxymethyl ether, dipropoxyundecenyl methoxymethyl ether, dibutoxyundecenyl methoxymethyl ether, dipentyloxyundecenyl methoxymethyl ether, dihexyloxyundecenyl methoxymethyl ether, diheptyloxyundecenyl methoxymethyl ether, dioctyloxyundecenyl methoxymethyl ether, dinonyloxyundecenyl methoxymethyl ether, and didecyloxyundecenyl methoxymethyl ether; dialkoxydodecenyl alkoxymethyl ether compounds such as dimethoxydodecenyl methoxymethyl ether, diethoxydodecenyl methoxymethyl ether, dipropoxydodecenyl methoxymethyl ether, dibutoxydodecenyl methoxymethyl ether, dipentyloxydodecenyl methoxymethyl ether, dihexyloxydodecenyl methoxymethyl ether, diheptyloxydodecenyl methoxymethyl ether, dioctyloxydodecenyl methoxymethyl ether, dinonyloxydodecenyl methoxymethyl ether, and didecyloxydodecenyl methoxymethyl ether; and dialkoxytridecenyl alkoxymethyl ether compounds such as dimethoxytridecenyl methoxymethyl ether, diethoxytridecenyl methoxymethyl ether, dipropoxytridecenyl methoxymethyl ether, dibutoxytridecenyl methoxymethyl ether, dipentyloxytridecenyl methoxymethyl ether, dihexyloxytridecenyl methoxymethyl ether, diheptyloxytridecenyl methoxymethyl ether, dioctyloxytridecenyl methoxymethyl ether, dinonyloxytridecenyl methoxymethyl ether, and didecyloxytridecenyl methoxymethyl ether.

The dialkoxyalkenyl alkoxymethyl ether compound (1) may be synthesized, for example, by acetalizing a terminal alkyne group of an alkoxymethyl alkynyl ether compound and catalytically reducing the carbon-carbon triple bond.

Next, the formylalkenyl alkoxymethyl ether compound (2) will be explained hereinafter.

In the general formula (2), $R^3$ and "a" are as defined for the general formula (1).

Specific examples of the formylalkenyl alkoxymethyl ether compound (2) include formylbutenyl alkoxymethyl ether compounds such as formylbutenyl methoxymethyl ether, formylbutenyl ethoxymethyl ether, formylbutenyl propoxymethyl ether, formylbutenyl butoxymethyl ether, formylbutenyl pentyloxymethyl ether, formylbutenyl hexyloxymethylether, formylbutenyl heptyloxymethyl ether, formylbutenyl octyloxymethyl ether, formylbutenyl nonyloxymethyl ether, formylbutenyl decyloxymethyl ether, and formylbutenyl benzyloxymethyl ether; formylpentenyl alkoxymethyl ether compounds such as formylpentenyl methoxymethyl ether, formylpentenyl ethoxymethyl ether, formylpentenyl propoxymethyl ether, formylpentenyl butoxymethyl ether, formylpentenyl pentyloxymethyl ether, formylpentenyl hexyloxymethyl ether, formylpentenyl heptyloxymethyl ether, formylpentenyl octyloxymethyl ether, formylpentenyl nonyloxymethyl ether, formylpentenyl decyloxymethyl ether, and formylpentenyl benzyloxymethyl ether; formylhexenyl alkoxymethyl ether compounds such as formylhexenyl methoxymethyl ether, formylhexenyl ethoxymethyl ether, formylhexenyl propoxymethyl ether, formylhexenyl butoxymethyl ether, formylhexenyl pentyloxymethyl ether, formylhexenyl hexyloxymethyl ether, formylhexenyl heptyloxymethyl ether, formylhexenyl octyloxymethyl ether, formylhexenyl nonyloxymethyl ether, formylhexenyl decyloxymethyl ether, and formylhexenyl benzyloxymethyl ether; formylheptenyl alkoxymethyl ether compounds such as formylheptenyl methoxymethyl ether, formylheptenyl ethoxymethyl ether, formylheptenyl propoxymethyl ether, formylheptenyl butoxymethyl ether, formylheptenyl pentyloxymethyl ether, formylheptenyl hexyloxymethyl ether, formylheptenyl heptyloxymethyl ether, formylheptenyl octyloxymethyl ether, formylheptenyl nonyloxymethyl ether, formylheptenyl decyloxymethyl ether, and formylheptenyl benzyloxymethyl ether; formyloctenyl alkoxymethyl ether compounds such as formyloctenyl methoxymethyl ether, formyloctenyl ethoxymethyl ether, formyloctenyl propoxymethyl ether, formyloctenyl butoxymethyl ether, formyloctenyl pentyloxymethyl ether, formyloctenyl hexyloxymethyl ether, formyloctenyl heptyloxymethyl ether, formyloctenyl octyloxymethyl ether, formyloctenyl nonyloxymethyl ether, formyloctenyl decyloxymethyl ether, and formyloctenyl benzyloxymethyl ether; formylnonenyl alkoxymethyl ether compounds such as formylnonenyl methoxymethyl ether, formylnonenyl ethoxymethyl ether, formylnonenyl propoxymethyl ether, formylnonenyl butoxymethyl ether, formylnonenyl pentyloxymethyl ether, formylnonenyl hexyloxymethyl ether, formylnonenyl heptyloxymethyl ether, formylnonenyl octyloxymethyl ether, formylnonenyl nonyloxymethyl ether, formylnonenyl decyloxymethyl ether, and formylnonenyl benzyloxymethyl ether; formyldecenyl alkoxymethyl ether compounds such as formyldecenyl methoxymethyl ether, formyldecenyl ethoxymethyl ether, formyldecenyl propoxymethyl ether, formyldecenyl butoxymethyl ether, formyldecenyl pentyloxymethyl ether, formyldecenyl hexyloxymethyl ether, formyldecenyl heptyloxymethyl ether, formyldecenyl octyloxymethyl ether, formyldecenyl nonyloxymethyl ether, formyldecenyl decyloxymethyl ether, and formyldecenyl benzyloxymethyl ether; formylundecenyl alkoxymethyl ether compounds such as formylundecenyl methoxymethyl ether, formylundecenyl ethoxymethyl ether, formylundecenyl propoxymethyl ether, formylundecenyl butoxymethyl ether, formylundecenyl pentyloxymethyl ether, formylundecenyl hexyloxymethyl ether, formylundecenyl heptyloxymethyl ether, formylundecenyl octyloxymethyl ether, formylundecenyl nonyloxymethyl ether, formylundecenyl decyloxymethyl ether, and formylundecenyl benzyloxymethyl ether; formyldodecenyl alkoxymethyl ether compounds such as formyldodecenyl methoxymethyl ether, formyldodecenyl ethoxymethyl ether, formyldodecenyl propoxymethyl ether, formyldodecenyl butoxymethyl ether, formyldodecenyl pentyloxymethyl ether, formyldodecenyl hexyloxymethyl ether, formyldodecenyl heptyloxymethyl ether, formyldodecenyl octyloxymethyl ether, formyldodecenyl nonyloxymethyl ether, formyldodecenyl decyloxymethyl ether, and formyldodecenyl benzyloxymethyl ether; and formyltridecenyl alkoxymethyl ether compounds such as formyltridecenyl methoxymethyl ether, formyltridecenyl ethoxymethyl ether, formyltridecenyl propoxymethyl ether, formyltridecenyl butoxymethyl ether, formyltridecenyl pentyloxymethyl ether, formyltridecenyl hexyloxymethyl ether, formyltridecenyl heptyloxymethyl ether, formyltridecenyl octyloxymethyl ether, formyltridecenyl nonyloxymethyl ether, formyltridecenyl decyloxymethyl ether, and formyltridecenyl benzyloxymethyl ether.

Next, the hydrolysis which the dialkoxyalkenyl alkoxymethyl ether compound (1) is subjected to will be explained hereinafter.

The hydrolysis may be carried out, for example, in the presence of an acid or water.

Examples of the acid include inorganic acids such as hydrochloric acid and hydrobromic acid; and p-toluenesulfonic acid (p-TsOH), benzenesulfonic acid, trifluoroacetic acid, acetic acid, formic acid, oxalic acid, iodotrimethylsilane, and titanium tetrachloride. p-Toluenesulfonic acid, acetic acid, formic acid, and hydrochloric acid are preferred, and formic acid and hydrochloric acid are more preferred, in view of the reactivity.

An amount of the acid used is preferably from 0.0001 to 2.0 mol, more preferably from 0.003 to 1.0 mol, per mol of the dialkoxyalkenyl alkoxymethyl ether compound (1) in view of the productivity.

The acid may be used alone or in combination thereof, if necessary. The acid may be commercially available one or may be prepared in house.

An amount of water used is preferably from 0 to 3000 g, more preferably from 0 to 300 g, per mol of the dialkoxyalkenyl alkoxymethyl ether compound (1), in view of the reactivity. When an acid to be used contains water, it may not be necessary to further add water.

The hydrolysis may be carried out in the absence of solvent or in the presence of solvent, if necessary. Carrying out the hydrolysis in the absence of a solvent makes a feed mass less and also makes it possible to avoid decrease in productivity.

Examples of the solvent include common solvents, for example, ethers such as dibutyl ether, 4-methyltetrahydropyran, cyclopentylmethylether, and 1,4-dioxane; hydrocarbons such as heptane, benzene, toluene, xylene, and cumene; chlorinated solvents such as trichloroethylene; aprotic polar solvents such as dimethyl sulfoxide, γ-butyrolactone, and hexamethylphosphoric triamide; nitriles such as acetonitrile and propionitrile; and esters such as n-propyl acetate and n-butyl acetate.

The solvent may be used alone or in combination thereof, if necessary. The solvent may be commercially available one.

Preferred solvents have a boiling point which is different from and higher than that of an alcohol formed in the hydrolysis (hereinafter referred to also as alcohol compound (7)).

An amount of the solvent used in the hydrolysis is preferably from 0 to 2000 g, more preferably from 0 to 500 g, per mol of the dialkoxyalkenyl alkoxymethyl ether compound (1).

A reaction temperature in the hydrolysis is preferably from 10 to 150° C., more preferably from 30 to 80° C., in view of the reactivity.

A reaction time in the hydrolysis varies, depending on a reaction scale and is preferably from 1 to 100 hours in view of the productivity.

Whether the hydrolysis is still progressing may be known, for example, by distilling off and weighing the alcohol compound (7) formed in the hydrolysis- or by monitoring the hydrolysis by GC. The former way is preferred in-view of safety and workability. More specifically in the former way, if weight of the alcohol distilled off is less than a theoretical weight of alcohol calculated on the basis of the amount of the fed starting material, dialkoxyalkenyl alkoxymethyl ether compound (1), and the weight is increasing with time, the hydrolysis is still progressing.

The present invention is particularly advantageous when the dialkoxyalkenyl alkoxymethyl ether compounds (1) is a formylalkenyl alkoxymethyl ether compound (2: a=1 to 4) having high solubility in water and having 4 to 7 carbon atoms. This is a case where a dialkoxybutenyl alkoxymethyl ether compound, a dialkoxypentenyl alkoxymethyl ether compound, a dialkoxyhexenyl alkoxymethyl ether compound, or a dialkoxyheptenyl alkoxymethyl ether compound is hydrolyzed to prepare the formylalkenyl alkoxymethyl ether compound (2: a=1 to 4), which is an aldehyde. Hereinafter, the preparation of a formylalkenyl alkoxymethyl ether compound (2: a=1 to 4) having 4 to 7 carbon atoms will be explained as an example. It should be noted that this does not mean that the preparation of a formylalkenyl alkoxymethyl ether compound (2: a=5 to 10) having 8 to 13 carbon atoms is precluded from the scope of the present invention.

Conventionally, when a formylalkenyl alkoxymethyl ether compound (2: a=1 to 4) is prepared by subjecting the dialkoxyalkenyl alkoxymethyl ether compound (1: a=1 to 4) to hydrolysis, it is necessary to use dichloromethane, chloroform, diethyl ether, toluene, or xylene, which are insoluble in water and has a high extraction ability, as a solvent in the reaction or as an extraction solvent. However, when such a solvent is used, the solvent should be separated by distillation, and, further, the solvent occupies a reactor volume to decrease an amount of raw materials to be fed. The separated solvent is a waste material, and may cause an environmental problem. Meanwhile, when such a solvent is not used, the formylalkenyl alkoxymethyl ether compound (2: a=1 to 4) transfers partly into the aqueous phase, resulting in an extremely low yield of the formylalkenyl alkoxymethyl ether compound (2: a=1 to 4). If alcohol is present in a reaction mixture containing the formylalkenyl alkoxymethyl ether compound (2: a=1 to 4), the solubility of the formylalkenyl alkoxymethyl ether compound (2: a=1 to 4) is increased in an aqueous phase, which leads to a greatly lowered yield, or fluctuation in a yield in repeated preparations even in the same conditions (see Comparative Examples 1 to 6 below).

In contrast, in the present invention, an alcohol formed in the hydrolysis is being removed during the progress of a hydrolysis, whereby partition of a formylalkenyl alkoxymethyl ether compound (2: a=1 to 4) having 4 to 7 carbon atoms from an aqueous phase into an aqueous phase is made less or zero, so that the formylalkenyl alkoxymethyl ether compound (2: a=1 to 4) is separated from the aqueous phase into the organic phase in a high yield and productivity (see, Examples 1 to 4 and Comparative Examples 1 to 6 below). The removal, during the hydrolysis, of an alcohol formed in the hydrolysis makes it possible to subject the reaction mixture as such to distillation to obtain a purified target compound, formylalkenyl alkoxymethyl ether compound (2: a=1 to 4), without post-treatments or with decreased post-treatment steps.

In the aforesaid hydrolysis, the dialkoxyalkenyl alkoxymethyl ether compound (1), acid and, optionally, water are fed in a reaction vessel and heated to distill off the alcohol compound (7) formed in the hydrolysis during the progress of the hydrolysis. When the alcohol compound (7) is ethanol, the distillation is carried out, for example, by increasing an internal temperature to 40 to 50° C. and then reducing the pressure to 235 mmHg (31.3 kPa) during the progress of the hydrolysis. The hydrolysis can be carried out by distilling off the alcohol compound (7) at normal pressure, but is preferably carried out at a reduced pressure in view of the thermostability of the formylalkenyl alkoxymethyl ether compound (2). Distillation of alcohol is continued by gradually reducing the pressure to 50 mmHg (6.67 kPa). When ethanol is not distilled off any more, the hydrolysis is judged to complete. A fact that ethanol is not distilled off any more may be determined by a fact that weight of a distillate does not change and is equal to weight of a theoretical amount of the alcohol compound (7) calculated from the amount of the starting dialkoxyalkenyl alkoxymethyl ether compound (1).

It is to be noted that the term "an internal temperature" means a temperature of the reaction mixture and is referred to also as a reaction temperature.

Specific examples of the alcohol compound (7) include linear alcohols such as methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol and n-pentadecanol; branched alcohols such as isopropanol and 2-butanol; and diols such as ethyleneglycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,2-propanediol, 2,2-dimethyl-1,3-propanediol and 2,2-dimethyl-1,4-butanediol.

The alcohol compound (7) recovered from the distillation has a high purity and, therefore, is reusable as a raw material for other reactions different from the present hydrolysis, such as acetalization of an aldehyde or dealkoxymethylation. Accordingly, the process according to the present invention is environmentally-friendly and economically very advantageous.

Thus, the formylalkenyl alkoxymethyl ether compound (2) may be prepared by subjecting the dialkoxyalkenyl alkoxymethyl ether compound (1) to hydrolysis in the presence of an acid, while removing an alcohol compound formed in the hydrolysis to thereby proceed further with the hydrolysis.

Next, will be described the process for preparing (5E,7Z)-5,7-dodecadiene-1-ol of the following formula (5) (hereinafter referred to also as (5E,7Z)-5,7-dodecadiene-1-ol (5)), which is a sex pheromone of *Thysanoplusia intermixta*, from the formylalkenyl alkoxymethyl ether compound (2: a=4) as obtained in the aforesaid preparation process.

The (5E,7Z)-5,7-dodecadiene-1-ol (5) may be prepared by subjecting the formylheptenyl alkoxymethyl ether compound (2: a=4) and a triarylphosphonium pentylide compound of the following general formula (3) (hereinafter referred to also as triarylphosphonium pentylide compound (3)) to a Wittig reaction to prepare a (5E,7Z)-5,7-dodecadienyl alkoxymethyl ether compound of the following formula (4: a=4) (hereinafter referred to also as (5E,7Z)-5,7-dodecadienyl alkoxymethyl ether (4: a=4)) and then subjecting the (5E,7Z)-5,7-dodecadienyl alkoxymethyl ether (4: a=4) to dealkoxymethylation.

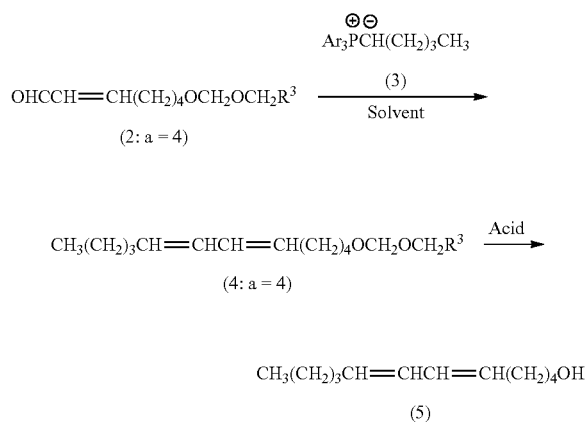

The Wittig reaction step will be now explained hereinafter.

In the general formula (3), Ar represents, independently of each other, an aryl group.

The aryl group has preferably 6 to 7 carbon atoms.

Examples of the aryl group include a phenyl group (Ph group (—C$_6$H$_5$)) and a tolyl group. A phenyl group is preferred in view of ease of synthesis, and more preferably, all of the three aryl groups are a phenyl group.

Specific examples of the triarylphosphonium pentylide compound (3) include triphenylphosphonium pentylide and tritolylphosphonium pentylide.

The triarylphosphonium pentylide compound (3) may be used alone or in combination thereof, if necessary.

The triarylphosphonium pentylide compound (3) may be prepared, for example, by reacting a 1-halopentane compound of the following general formula (8) (hereinafter referred to also as 1-halopentane compound (8)) with a phosphorus compound of the following general formula (9) (hereinafter referred to also as phosphorus compound (9)) to form a pentynyltriarylphosphonium halide compound of the following general formula (10) (hereinafter referred to also as pentynyltriarylphosphonium halide compound (10)) and, then, subjecting the pentynyltriarylphosphonium halide compound (10) to deprotonation with a base to form a triarylphosphonium pentylide compound (3).

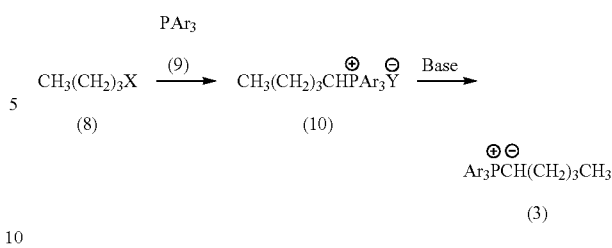

X in the 1-halopentane compound (8) represents a halogen atom. Examples of the halogen atom include a chlorine atom, a bromine atom, and an iodine atom. A chlorine atom and a bromine atom are preferred in view of the versatility.

Specific examples of the 1-halopentane compound (8) include 1-chloropentane, 1-bromopentane, and 1-iodopentane.

In the general formula (9), Ar is as defined for the general formula (3).

Specific examples of the phosphorus compound (9) include triarylphosphine compounds such as triphenylphosphine and tritolylphosphine. Triphenylphosphine is preferred in view of the reactivity.

An amount of the phosphorus compound (9) used is preferably from 0.8 to 5.0 mol per mol of the 1-halopentane compound (8) in view of the reactivity.

A halide may be incorporated in the reaction mixture for the preparation of the pentyltriarylphosphonium halide compound (10), if necessary.

Examples of the halide include sodium iodide, potassium iodide, sodium bromide, and potassium bromide. Iodides such as sodium iodide and potassium iodide are preferred in view of the reactivity.

The halide may be used alone or in combination thereof, if necessary. The halide may be commercially available one.

An amount of the halide used is preferably from 0 to 5.0 mol per mol of the 1-halopentane compound (8) in view of the reactivity.

A base may be incorporated in the reaction mixture for the preparation of the pentyltriarylphosphonium halide compound (10), if necessary.

Examples of the base include alkaline metal carbonates such as potassium carbonate and sodium carbonate; alkaline earth metal carbonates such as calcium carbonate and magnesium carbonate; and amines such as triethylamine, tripropylamine, triisopropylamine, tributylamine, N,N-diethylaniline, and pyridine. The alkaline metal carbonates are preferred in view of the handling.

The base may be used alone or in combination thereof, if necessary. The base may be commercially available one.

An amount of the base used is preferably from 0 to 2.0 mol per mol of the 1-halopentane compound (8) in view of the reactivity.

A reaction temperature (optimal temperature) in the preparation of the pentyltriarylphosphonium halide compound (10) varies, depending on a solvent used, and is preferably from 60 to 180° C.

A reaction time in the preparation of the pentyltriarylphosphonium halide compound (10) varies, depending on a solvent used and a production scale, and is preferably from 0.5 to for 55 hours.

Y in the general formula (10) represents a halogen atom. Examples of the halogen atom include a chlorine atom, a bromine atom, and an iodine atom.

When no halide is used in the preparation of the pentyltriarylphosphonium halide compound (10), Y is the same halogen atom as X in the general formula (8). When an iodide is used as a halide in the preparation, Y is the same halogen atom as X described above or an iodine atom.

In the general formula (10), Ar is as defined for the general formula (3).

Specific examples of the pentyltriarylphosphonium halide compound (10) include pentyltriphenylphosphonium halide compounds such as pentyltriphenylphosphonium chloride, pentyltriphenylphosphonium bromide, and pentyltriphenylphosphonium iodide; and pentyltritolylphosphonium halide compounds such as pentyltritolylphosphonium chloride, pentyltritolylphosphonium bromide, and pentyltritolylphosphonium iodide.

The triarylphosphonium pentylide compound (3) may be prepared by adding a base to the reaction system in which the pentyltriarylphosphonium halide (10) has been prepared to cause deprotonation to directly obtain the triarylphosphonium pentylide compound (3) or by isolating and purifying the pentyltriarylphosphonium halide (10) and then cause deprotonation with a base to obtain the triarylphosphonium pentylide compound (3).

Examples of the base used in the deprotonation of the pentyltriarylphosphonium halide (10) include alkyllithiums such as n-butyl lithium and tert-butyl lithium; organometallic reagents such as methylmagnesium chloride, methylmagnesium bromide, sodium acetylide, and potassium acetylide; metal alkoxides such as potassium tert-butoxide, sodium tert-butoxide, potassium methoxide, sodium methoxide, potassium ethoxide, and sodium ethoxide; and metal amides such as lithium diisopropylamide and sodium bis(trimethylsilyl)amide. Metal alkoxides are preferred, and potassium tert-butoxide, sodium methoxide, and sodium ethoxide are more preferred in view of the reactivity.

An amount of the base used is preferably from 0.7 to 5.0 mol per mol of the 1-halopentane compound (8) in view of the reactivity.

A reaction temperature (optimal temperature) in the deprotonation of the pentyltriarylphosphonium halide (10) varies, depending on a solvent and a base used and is preferably from −78 to 40° C.

A reaction time in the deprotonation of the pentyltriarylphosphonium halide (10) varies, depending on a solvent used and a production scale and is preferably from 0.5 to 50 hours.

A solvent may be used in the preparation of the pentyltriarylphosphonium halide compound (10) and in the deprotonation of the pentyltriarylphosphonium halide (10), if necessary.

Examples of the solvent include ether-type solvents such as tetrahydrofuran, diethyl ether, dibutyl ether, 4-methyltetrahydropyran, cyclopentylmethylether, and 1,4-dioxane; hydrocarbon-type solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Ether solvents such as tetrahydrofuran and 4-methyltetrahydropyran and polar solvents such as acetonitrile, N,N-dimethylformamide, and N,N-dimethylacetamide are preferred in view of the reactivity.

The solvent may be used alone or in combination thereof, if necessary. The solvent may be commercially available one.

An amount of the solvent used is preferably from 10 to 6000 g, more preferably from 50 to 4000 g, per mol of the 1-halopentane compound (8) or the pentyltriarylphosphonium halide compound (10) in view of the reactivity.

An amount of the triarylphosphonium pentylide compound (3) used is preferably from 1.0 to 4.0 mol, more preferably from 1.0 to 2.0 mol, per mol of the formylalkenyl alkoxymethyl ether compound (2) in view of the reactivity.

A solvent may be used in the Wittig reaction, if necessary.

Examples of the solvent include ether solvents such as tetrahydrofuran, diethyl ether, dibutyl ether, 4-methyltetrahydropyran, cyclopentylmethylether, and 1,4-dioxane; hydrocarbon-type solvents such as hexane, heptane, benzene, toluene, xylene, and cumene; and polar solvents such as N,N-dimethylformamide, N,N-dimethylacetamide, N-methylpyrrolidone, dimethyl sulfoxide, γ-butyrolactone, acetonitrile, dichloromethane, and chloroform. Ether solvents such as tetrahydrofuran and 4-methyltetrahydropyran and polar solvents such as acetonitrile, N,N-dimethylformamide, and N,N-dimethylacetamide are preferred in view of the reactivity.

The solvent may be used alone or in combination thereof, if necessary. The solvent may be commercially available one.

An amount of the solvent used is preferably from 10 to 6000 g, more preferably from 50 to 4000 g, per mol of the formylalkenyl alkoxymethyl ether compound (2) in view of the reactivity.

An optimal reaction temperature of the Wittig reaction varies, depending on a solvent used and is preferably from −78 to 40° C.

The reaction time of the Wittig reaction varies, depending on a reaction scale and is preferably from 0.5 to 50 hours.

Specific examples of the (5E,7Z)-5,7-dodecadienyl alkoxymethyl ether compound (4) include (5E,7Z)-5,7-dodecadienyl methoxymethyl ether, (5E,7Z)-5,7-dodecadienyl ethoxymethyl ether, (5E,7Z)-5,7-dodecadienyl propoxymethyl ether, (5E,7Z)-5,7-dodecadienyl butoxymethyl ether, (5E,7Z)-5,7-dodecadienyl pentyloxymethyl ether, (5E,7Z)-5,7-dodecadienyl hexyloxymethyl ether, (5E,7Z)-5,7-dodecadienyl heptyloxymethyl ether, (5E,7Z)-5,7-dodecadienyl octyloxymethyl ether, (5E,7Z)-5,7-dodecadienyl nonyloxymethyl ether, (5E,7Z)-5,7-dodecadienyl decyloxymethyl ether, and (5E,7Z)-5,7-dodecadienyl benzyloxymethyl ether.

Next, the dealkoxymethylation step will be explained.

The dealkoxymethylation of the (5E,7Z)-5,7-dodecadienyl alkoxymethyl ether compound (4: a=4) may be carried out using, for example, an acid and an alcohol compound of the following general formula (11) (hereinafter referred to also as alcohol compound (11)).

$$R^4OH \quad (11)$$

Examples of the acid used in the dealkoxymethylation include inorganic acids such as hydrochloric acid and hydrobromic acid; and p-toluenesulfonic acid (p-TsOH), benzenesulfonic acid, trifluoroacetic acid, acetic acid, formic acid, oxalic acid, iodotrimethylsilane, and titanium tetrachloride. p-Toluenesulfonic acid and hydrochloric acid are preferred in view of the reactivity.

The acid may be used alone or in combination thereof, if necessary. The acid may be commercially available one.

An amount of the acid used is preferably from 0.001 to 10.0 mol, more preferably from 0.01 to 3.0 mol, per mol of the (5E,7Z)-5,7-dodecadienyl alkoxymethyl ether compound (4) in view of the completion of the reaction.

In the general formula (11), $R^4$ represents a monovalent hydrocarbon having 1 to 15 carbon atoms, preferably having 1 to 6 carbon atoms in view of the price or versatility. The monovalent hydrocarbon group is the same as the monovalent hydrocarbon group of $R^1$ and $R^2$ in the general formula (1).

Examples of the alcohol compound (11) include linear alcohols such as methanol, ethanol, n-propanol, n-butanol, n-pentanol, n-hexanol, n-heptanol, n-octanol, n-nonanol, n-decanol, n-undecanol, n-dodecanol, n-tridecanol, n-tetradecanol, and n-pentadecanol; and branched alcohols such as isopropanol and 2-butanol. Methanol and ethanol are preferred in view of the reactivity.

The alcohol compound (11) may be used in combination thereof, if necessary.

The alcohol compound (11) may be commercially available one or the alcohol compound (7) recovered in the hydrolysis.

An amount of the alcohol compound (11) used is preferably from 1.0 to 100 mol, more preferably from 1.0 to 40 mol, per mol of the (5E,7Z)-5,7-dodecadienyl alkoxymethyl ether compound (4) in view of the reactivity.

A solvent may be used besides the alcohol compound (11) in the dealkoxymethylation, if necessary.

Examples of the solvent include common solvents, for example, ethers such as dibutyl ether, 4-methyltetrahydropyran, cyclopentylmethylether, and 1,4-dioxane; hydrocarbons such as heptane, benzene, toluene, xylene, and cumene; chlorinated solvents such as trichloroethylene; aprotic polar solvents such as dimethyl sulfoxide, γ-butyrolactone, and hexamethylphosphoric triamide; nitriles such as acetonitrile and propionitrile; and esters such as n-propyl acetate and n-butyl acetate.

The solvent may be used alone or in combination thereof, if necessary. The solvent may be commercially available one.

An amount of the solvent used in the dealkoxymethylation is preferably from 0 to 2000 g, more preferably from 0 to 500 g, per mol of the (5E,7Z)-5,7-dodecadienyl alkoxymethyl ether compound (4).

The solvent occupies an inner space of a reactor to decrease a space for the raw materials so as to decrease productivity. Therefore, the reaction may be carried out without using the solvent.

A (5E,7Z)-5,7-dodecadienyl acetate of the following formula (6) (hereinafter referred to also as (5E,7Z)-5,7-dodecadienyl acetate (6)) may be prepared by acetylation of the (5E,7Z)-5,7-dodecadiene-1-ol (5) obtained in the aforesaid process.

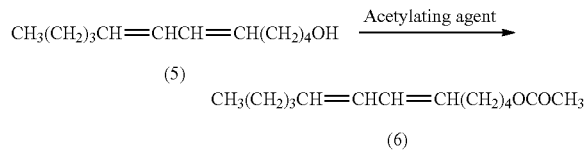

The acetylation of the (5E,7Z)-5,7-dodecadiene-1-ol (5) may be carried out using, for example, an acetylating agent.

Examples of the acetylating agent include acid anhydrides such as acetic anhydride; acetyl halide compounds such as acetyl chloride, acetyl bromide, and acetyl iodide; and acetic ester compounds such as methyl acetate and ethyl acetate. Acetic anhydride and acetyl halide compounds are preferred in view of the versatility.

An amount of the acetylating agent used is preferably from 1.0 to 10.0 mol, more preferably from 1.0 to 5.0 mol, per mol of the (5E,7Z)-5,7-dodecadiene-1-ol (5) in view of the reactivity and cost efficiency.

An acid or base may be used in the acetylation, if necessary.

Examples of the acid include mineral acids such as hydrochloric acid, sulfuric acid, and nitric acid; aromatic sulfonic acids such as benzenesulfonic acid and p-toluenesulfonic acid; and Lewis acids such as boron trifluoride etherate and tetraisopropyl orthotitanate.

The acid may be used alone or in combination thereof, if necessary.

An amount of the acid used is preferably from 0.01 to 1.00 mol, more preferably from 0.01 to 0.50 mol, per mol of the (5E,7Z)-5,7-dodecadiene-1-ol (5) in view of the reactivity and cost efficiency.

Examples of the base include trialkylamines such as trimethylamine, triethylamine, and N,N-diisopropylethylamine; aromatic amine compounds such as pyridine, N,N-dimethylaniline, N,N-diethylaniline, and 4-dimethylaminopyridine; and metal alkoxides such as potassium t-butoxide, sodium methoxide, and sodium ethoxide.

The base may be used alone or in combination thereof, if necessary.

An amount of the base used is preferably from 1.0 to 10.0 mol, more preferably from 1.0 to 3.0 mol, per mol of the (5E,7Z)-5,7-dodecadiene-1-ol (5) in view of the reactivity and cost efficiency.

A solvent may be used in the acetylation, if necessary.

Examples of the solvent include common solvents, for example, ethers such as tetrahydrofuran, diethyl ether, dibutyl ether, 4-methyltetrahydropyran, cyclopentylmethylether, and 1,4-dioxane; hydrocarbons such as heptane, benzene, toluene, xylene, and cumene; chlorinated solvents such as dichloromethane, chloroform, and trichloroethylene; aprotic polar solvents such as dimethyl sulfoxide, γ-butyrolactone, N-methylpyrrolidone, and hexamethylphosphoric triamide; nitriles such as acetonitrile and propionitrile; and esters such as methyl acetate, ethyl acetate, n-propyl acetate, and n-butyl acetate. Hydrocarbons such as toluene and xylene are preferred.

The solvent may be used alone or in combination thereof, if necessary. The solvent may be commercially available one.

An amount of the solvent used in the acetylation is preferably from 0 to 2000 g, more preferably from 0 to 500 g, per mol of the (5E,7Z)-5,7-dodecadiene-1-ol (5).

Thus, there is provided the process for preparing (5E,7Z)-5,7-dodecadiene-1-ol (5) and (5E,7Z)-5,7-dodecadienyl acetate (6), which are sex pheromones of *Thysanoplusia intermixta*, from the formylalkenyl alkoxymethyl ether compound (2: a=4).

EXAMPLES

The present invention will be described in details with reference to the following Examples. It should be construed that the present invention is not limited to or by the following Examples.

The term "purity" as used herein means an area percentage determined by gas chromatography (GC), unless otherwise specified. The term "production ratio" means a ratio of area percentages determined by GC. The term "yield" is calculated from the area percentages determined by GC.

In the Examples, monitoring of the reactions was carried out in the following GC conditions.

GC conditions: GC: Capillary gas chromatograph GC-2014 (Shimadzu Corporation); column: DB-WAX, 0.25 mm×0.25 mmϕ×30 m; carrier gas: He (1.55 mL/min), detector: FID; column temperature: 150° C., elevated by 5° C./min, up to 230° C.

Yield was calculated by the following equation in consideration of purities (% GC) of a raw material and a product.

Yield (%)={[(mass of a product obtained in a reaction×% GC)/molecular mass of a product]±[(mass of a raw material in a reaction×% GC)/molecular mass of a raw material]}×100

Example 1: Preparation of formylpentenyl methoxymethyl ether (2: $R^3$=H; a=2), $CH_3OCH_2O(CH_2)_2CH=CHCHO$

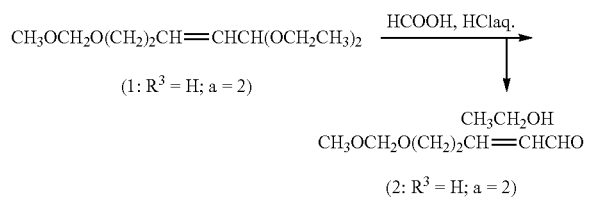

Diethoxypentenyl methoxymethyl ether (1: $R^3$=H; a=2) (795.07 g, 3.54 mol, purity 97.05%) and water (106.32 g, 5.90 mol) were placed in a reactor at room temperature and stirred at 30 to 40° C. for 1 hour. After the completion of stirring, formic acid (8.14 g, 0.16 mol, purity 88%) was added dropwise at 30 to 45° C. to cause hydrolysis. Subsequently, 20 mass % hydrochloric acid (0.64 g, 0.0035 mol of hydrogen chloride) was added dropwise at 30 to 45° C. and stirred at 40 to 45° C. for 30 minutes.

Subsequently, the pressure was reduced to 235 mmHg (31.3 kPa) and then gradually to 50 mmHg (6.67 kPa) at an internal temperature of 40 to 55° C. in the progress of the hydrolysis, wherein ethanol formed in the hydrolysis (325.85 g, 7.01 mol, purity 99.11%) was distilled off and removed. No distillate occurred any more 4 hours after the start of the depressurization. Then, toluene (557.04 g), water (218.20 g), sodium chloride (65.00 g), and 20 mass % hydrochloric acid (12.89 g, 0.071 mol of hydrogen chloride) were added to cause phase separation. The aqueous phase was removed to obtain the organic phase. Then, the resulting organic phase was washed with brine, followed by phase separation. The aqueous phase was removed to obtain the organic phase. The resulting organic phase was further washed with an aqueous solution of sodium bicarbonate, followed by phase separation. The aqueous phase was removed to obtain the organic phase. The resulting organic phase was subjected to distillation at a reduced pressure to obtain formylpentenyl methoxymethyl ether (2: $R^3$=H; a=2) (496.73 g, 3.29 mol, purity 95.41%, b.p.=87.2 to 87.6° C./3.0 mmHg (0.40 kPa)) in a yield of 93.00%.

The progress of the hydrolysis was confirmed by measuring the amount of ethanol distilled off. Specifically, the theoretical amount of ethanol formed in the hydrolysis is 326.18 g=3.54 mol of the starting material, diethoxypentenyl methoxymethyl ether (1: $R^3$=H; a=2)),×46.07 (molecular mass of ethanol)×2 (number of alcohol moieties per molecule of the starting material); when the amount of ethanol formed in the hydrolysis was less than the theoretical amount, the hydrolysis was judged to be still proceeding. When the amount of ethanol formed became 325.85 g as described above, which is substantially same as the theoretical amount, and did not increase any more, the hydrolysis was judged to be complete.

Formylpentenyl methoxymethyl ether (2: $R^3$=H; a=2)

Nuclear magnetic resonance spectrum: $^1$H-NMR (500 MHz, $CDCl_3$): δ=2.61 (2H, ddt, J=1.6 Hz, 6.5 Hz, 6.5 Hz), 3.23 (3H, s), 3.68 (2H, t, J=6.2 Hz), 4.60 (2H, s), 6.16 (1H, ddt, J=15.6 Hz, 10.7 Hz, 1.6 Hz), 6.86 (1H, dt, J=15.6 Hz, 6.5 Hz), 9.49 (1H, d, J=11.0 Hz); $^{13}$C-NMR (500 MHz, $CDCl_3$): δ=32.94, 55.27, 65.40, 96.40, 134.19, 154.87, 193.75.

Mass spectrum: EI-mass spectrum (70 eV): m/z 114 ($M^+$-30), 99, 83, 75, 55, 45.

Infrared absorption spectrum (NaCl): ν=2934, 2886, 2824, 1691, 1151, 1110, 1043, 974, 918.

Example 2: Preparation of formylpentenyl methoxymethyl ether (2: $R^3$=H; a=2), $CH_3OCH_2O(CH_2)_2CH=CHCHO$

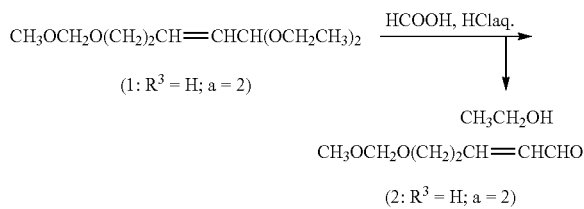

Diethoxypentenyl methoxymethyl ether (1: $R^3$=H; a=2) (283.84 g, 1.26 mol, purity 97.05%) and water (37.96 g, 2.11 mol) were placed in a reactor at room temperature and stirred at 30 to 40° C. for 22 minutes. After the completion of stirring, formic acid (2.56 g, 0.049 mol, purity 88%) was added dropwise at 30 to 45° C. to cause hydrolysis. Subsequently, 20 mass % hydrochloric acid (0.23 g, 0.0013 mol of hydrogen chloride) was added dropwise at 30 to 45° C. and stirred at 40 to 45° C. for 100 minutes.

Subsequently, the pressure was reduced to 235 mmHg (31.3 kPa) and then gradually to 50 mmHg (6.67 kPa) at an internal temperature of 40 to 55° C. in the progress of the hydrolysis, wherein ethanol formed in the hydrolysis (123.12 g, 2.61 mol, purity 97.51%) was distilled off and removed. No distillate occurred any more 4 hours after the start of the depressurization. Then, the pressure was further reduced to 3.0 mmHg (0.40 kPa), and the reaction mixture was subjected to distillation at a reduced pressure to obtain formylpentenyl methoxymethyl ether (2: $R^3$=H; a=2) (182.44 g, 1.20 mol, purity 94.59%, b.p.=87.6 to 88.6° C./3.0 mmHg (0.40 kPa)) in a yield of 94.88%.

The progress of the hydrolysis was confirmed in the same method as in Example 1.

Various spectrum data of the formylpentenyl methoxymethyl ether thus prepared were the same as those obtained in Example 1.

Comparative Example 1: Preparation of formylpentenyl methoxymethyl ether (2: $R^3$=H; a=2), $CH_3OCH_2O(CH_2)_2CH$=$CHCHO$

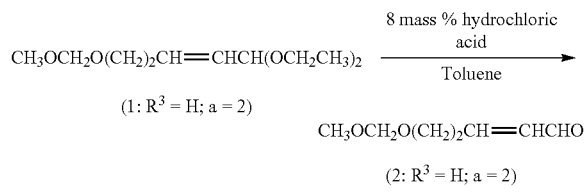

Diethoxypentenyl methoxymethyl ether (1: $R^3$=H; a=2) (283.84 g, 1.26 mol, purity 97.05%) and toluene (80.00 g) were placed in a reactor at room temperature and stirred at 10 to 15° C. for 6 minutes. After the completion of stirring, 8 mass % hydrochloric acid (145.13 g, 0.32 mol of hydrogen chloride) was added dropwise at 15 to 20° C. to cause hydrolysis. The progress of hydrolysis was monitored by GC at 15 to 20° C. After a conversion was confirmed to be 99.5% or more, the reaction was stopped. The reaction time from the dropwise addition of 8 mass % hydrochloric acid to the termination of the reaction was 1 hour. Toluene (200.00 g) was further added to the reaction mixture, followed by phase separation. The aqueous phase was then removed to obtain the organic phase. Then, the resulting organic phase was washed with brine, followed by phase separation. The aqueous phase was then removed to obtain the organic phase. The resulting organic phase was further washed with an aqueous solution of sodium bicarbonate, followed by phase separation. The aqueous phase was then removed to obtain the organic phase. The resulting organic phase was subjected to distillation at a reduced pressure to obtain formylpentenyl methoxymethyl ether (2: $R^3$=H; a=2) (131.78 g, 0.84 mol, purity 91.47%, b.p.=87.2 to 87.6° C./3.0 mmHg (0.40 kPa)) in a yield of 66.25%. Each of the removed aqueous phases contained ethanol formed in the hydrolysis.

Various spectrum data of the formylpentenyl methoxymethyl ether thus prepared were the same as those obtained in Example 1.

Comparative Example 2: Preparation of formylpentenyl methoxymethyl ether (2: $R^3$=H; a=2), $CH_3OCH_2O(CH_2)_2CH$=$CHCHO$

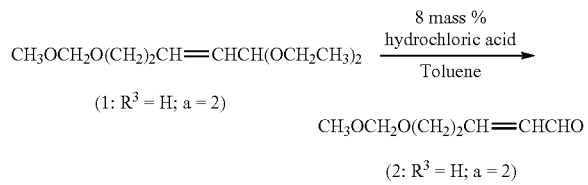

The procedures of Comparative Example 1 were repeated to obtain formylpentenyl methoxymethyl ether (2: $R^3$=H; a=2) (171.49 g, 1.06 mol, purity 89.12%, b.p.=87.2 to 87.6° C./3.0 mmHg (0.40 kPa)) in a yield of 84.00%. Although Comparative Examples 1 and 2 were carried out in the same conditions, the yield was 66.25% in Comparative Example 1 and 84.00% in Comparative Example 2. Thus, the yield varied.

Various spectrum data of the formylpentenyl methoxymethyl ether thus prepared were the same as those obtained in Example 1.

Comparative Example 3: Preparation of formylpentenyl methoxymethyl ether (2: $R^3$=H; a=2), $CH_3OCH_2O(CH_2)_2CH$=$CHCHO$

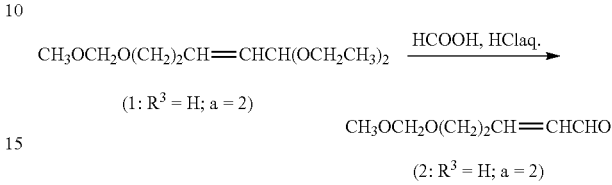

Diethoxypentenyl methoxymethyl ether (1: $R^3$=H; a=2) (283.84 g, 1.26 mol, purity 97.05%) and water (37.96 g, 2.11 mol) were placed in a reactor at room temperature and stirred at 30 to 40° C. for 1 hour. After the completion of stirring, formic acid (2.56 g, 0.049 mol, purity 88%) was added dropwise at 30 to 45° C. to cause hydrolysis. Subsequently, 20 mass % hydrochloric acid (0.23 g, 0.0013 mol of hydrogen chloride) was added dropwise at 30 to 45° C. and stirred at 40 to 45° C. for 30 minutes.

Subsequently, the progress of the hydrolysis was monitored by GC at an internal temperature of 40 to 55° C. After a conversion was confirmed to be 99.5% or more, the reaction was stopped. The reaction time from the dropwise addition of 20 mass % hydrochloric acid to the termination of the reaction was 4.5 hours. Toluene (200.00 g) was further added to the reaction mixture, followed by phase separation. The aqueous phase was then removed to obtain the organic phase. Then, the resulting organic phase was washed with brine, followed by phase separation. The aqueous phase was then removed to obtain the organic phase. The resulting organic phase was further washed with an aqueous solution of sodium bicarbonate, followed by phase separation. The aqueous phase was then removed to obtain the organic phase. The resulting organic phase was subjected to distillation at a reduced pressure to obtain formylpentenyl methoxymethyl ether (2: $R^3$=H; a=2) (149.40 g, 0.93 mol, purity 90.10%, b.p.=82.6 to 85.4° C./3.0 mmHg (0.40 kPa)) in a yield of 73.98%. Although Comparative Example 3 was carried out in the same conditions as in Example 1, except the distillation-off and removal of ethanol, Comparative Example 3 resulted in a yield of 73.98% and a purity of 90.10% which were lower than the yield of 93.00% and the purity of 95.41% in Example 1.

Various spectrum data of the formylpentenyl methoxymethyl ether thus prepared were the same as those obtained in Example 1.

Example 3: Preparation of formylpentenyl ethoxymethyl ether (2: $R^3$=$CH_3$; a=2), $CH_3CH_2OCH_2O(CH_2)_2CH$=$CHCHO$

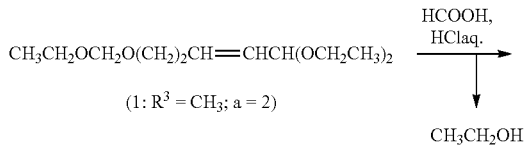

-continued $$CH_3CH_2OCH_2O(CH_2)_2CH=CHCHO$$

Diethoxypentenyl methoxymethyl ether (1: $R^3$=CH$_3$; a=2) (308.10 g, 1.26 mol, purity 95.16%) and water (37.96 g, 2.11 mol) were placed in a reactor at room temperature and stirred at 30 to 40° C. for 22 minutes. After the completion of stirring, formic acid (2.56 g, 0.049 mol, purity 88%) was added dropwise at 30 to 45° C. to cause hydrolysis. Subsequently, 20 mass % hydrochloric acid (0.23 g, 0.0013 mol of hydrogen chloride) was added dropwise at 30 to 45° C. and stirred at 40 to 45° C. for 60 minutes.

Subsequently, the pressure was reduced to 235 mmHg (31.3 kPa) and then gradually to 50 mmHg (6.67 kPa) at an internal temperature of 40 to 55° C. during the progress of the hydrolysis. Ethanol formed in the hydrolysis (119.02 g, 2.53 mol, purity 97.75%) was distilled off and removed. No distillate occurred any more 4 hours after the start of the depressurization. Then, toluene (234.56 g), water (77.90 g), sodium chloride (23.21 g), and 20 mass % hydrochloric acid (4.60 g, 0.025 mol of hydrogen chloride) were added to cause phase separation. The aqueous phase was removed to obtain the organic phase. Then, the resulting organic phase was washed with brine, followed by phase separation. The aqueous phase was then removed to obtain the organic phase. The resulting organic phase was further washed with an aqueous solution of sodium bicarbonate, followed by phase separation. The aqueous phase was then removed to obtain the organic phase. The resulting organic phase was subjected to distillation at a reduced pressure to obtain formylpentenyl ethoxymethyl ether (2: $R^3$=CH$_3$; a=2) (197.56 g, 1.139 mol, purity 91.20%, b.p.=85.0 to 86.1° C./3.0 mmHg (0.40 kPa)) in a yield of 90.26%.

The progress of the hydrolysis was confirmed in the same method as in Example 1.

Formylpentenyl ethoxymethyl ether (2: $R^3$=CH$_3$; a=2)

Nuclear magnetic resonance spectrum: $^1$H-NMR (500 MHz, CDCl$_3$): δ=1.19 (3H, t, J=6.9 Hz), 2.60 (2H, ddt, J=15.6 Hz, 6.5 Hz, 6.5 Hz), 3.56 (2H, q, J=6.9 Hz), 3.69 (2H, t, J=6.5 Hz), 4.65 (2H, s), 6.16 (1H, ddt, J=15.6 Hz, 8.1 Hz, 1.5 Hz), 6.85 (1H, dt, J=15.6 Hz, 6.5 Hz), 9.49 (1H, d, J=8.0 Hz); $^{13}$C-NMR (500 MHz, CDCl$_3$): δ=15.05, 32.96, 63.34, 65.40, 95.07, 134.17, 154.96, 193.76

Mass spectrum: EI-mass spectrum (70 eV): m/z 128 (M$^+$-30), 113, 98, 83, 70, 59, 41.

Infrared absorption spectrum (NaCl): ν=2976, 2931, 2878, 1692, 1114, 1099, 1042, 975, 847.

Comparative Example 4: Preparation of formylpentenyl ethoxymethyl ether (2: $R^3$=CH$_3$; a=2), $CH_3CH_2OCH_2O(CH_2)_2CH=CHCHO$

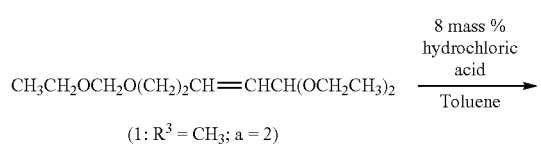

-continued $$CH_3CH_2OCH_2O(CH_2)_2CH=CHCHO$$

Diethoxypentenyl ethoxymethyl ether (1: $R^3$=CH$_3$; a=2) (308.10 g, 1.26 mol, purity 95.16%) and toluene (80.00 g) were placed in a reactor at room temperature and stirred at 10 to 15° C. for 31 minutes. After the completion of stirring, 8 mass % hydrochloric acid (145.13 g, 0.32 mol of hydrogen chloride) was added dropwise at 15 to 20° C. to cause hydrolysis. The progress of hydrolysis was monitored by GC at 15 to 20° C. After a conversion was confirmed to be 99.5% or more, the reaction was stopped. The reaction time from the dropwise addition of 8 mass % hydrochloric acid to the termination of the reaction was 1 hour. Toluene (200.00 g) was further added to the reaction mixture, followed by phase separation. The aqueous phase was then removed to obtain the organic phase. Then, the resulting organic phase was washed with brine, followed by phase separation. The aqueous phase was then removed to obtain the organic phase. The resulting organic phase was further washed with an aqueous solution of sodium bicarbonate, followed by phase separation. The aqueous phase was then removed to obtain the organic phase. The resulting organic phase was subjected to distillation at a reduced pressure to obtain formylpentenyl ethoxymethyl ether (2: $R^3$=CH$_3$; a=2) (141.18 g, 0.74 mol, purity 82.61%, b.p.=85.0 to 86.1° C./3.0 mmHg (0.40 kPa)) in a yield of 58.42%. Each of the removed aqueous phases contained ethanol formed in the hydrolysis.

Various spectrum data of the formylpentenyl ethoxymethyl ether (2: $R^3$=CH$_3$; a=2) thus prepared were the same as those obtained in Example 3.

Comparative Example 5: Preparation of formylpentenyl ethoxymethyl ether (2: $R^3$=CH$_3$; a=2), $CH_3CH_2OCH_2O(CH_2)_2CH=CHCHO$

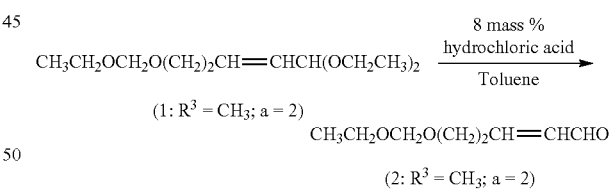

The procedures of Comparative Example 4 were repeated to obtain formylpentenyl ethoxymethyl ether (2: $R^3$=CH$_3$; a=2) (171.46 g, 0.90 mol, purity 82.91%, b.p.=85.0 to 86.1° C./3.0 mmHg (0.40 kPa)) in a yield of 71.21%. Although Comparative Examples 4 and 5 were carried out in the same conditions, the yield was 58.42% in Comparative Example 4 and 71.21% in Comparative Example 5. Thus, the yield varied.

Various spectrum data of the formylpentenyl ethoxymethyl ether (2: $R^3$=CH$_3$; a=2) thus prepared were the same as those obtained in Example 3.

Example 4: Preparation of Formylheptenyl methoxymethyl ether (2: $R^3$=H; a=4), $CH_3OCH_2O(CH_2)_4CH$=$CHCHO$

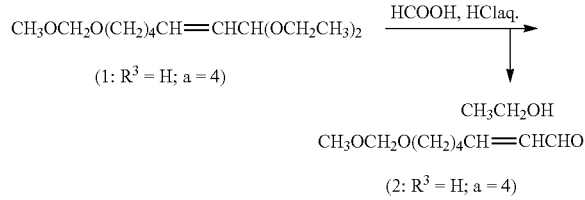

Diethoxyheptenyl methoxymethyl ether (1: $R^3$=H; a=4) (500.00 g, 1.95 mol, purity 95.97%) and water (58.60 g, 3.25 mol) were placed in a reactor at room temperature and stirred at 30 to 40° C. for 12 minutes. After the completion of stirring, formic acid (3.95 g, 0.076 mol, purity 88%) was added dropwise at 30 to 45° C. to cause hydrolysis. Subsequently, 20 mass % hydrochloric acid (0.35 g, 0.0019 mol of hydrogen chloride) was added dropwise at 30 to 45° C. and stirred at 40 to 45° C. for 104 minutes.

Subsequently, the pressure was reduced to 235 mmHg (31.3 kPa) and then gradually to 50 mmHg (6.67 kPa) at an internal temperature of 40 to 55° C. during the progress of the hydrolysis. Ethanol formed in the hydrolysis (192.43 g, 4.12 mol, purity 98.74%) was distilled off and removed. No distillate occurred any more 4.5 hours after the start of the depressurization. Then, toluene (362.06 g), water (120.25 g), sodium chloride (35.83 g), and 20 mass % hydrochloric acid (7.10 g, 0.039 mol of hydrogen chloride) were added to cause phase separation. The aqueous phase was then removed to obtain the organic phase. Then, the resulting organic phase was washed with brine, followed by phase separation. The aqueous phase was then removed to obtain the organic phase. The resulting organic phase was further washed with an aqueous solution of sodium bicarbonate, followed by phase separation. The aqueous phase was then removed to obtain the organic phase. The resulting organic phase was subjected to distillation at a reduced pressure to obtain formylheptenyl methoxymethyl ether (2: $R^3$=H; a=4) (340.59 g, 1.83 mol, purity 92.73%, b.p.=108.2 to 109.8° C./3.0 mmHg (0.40 kPa)) in a yield of 94.14%.

The progress of the hydrolysis was confirmed in the same method as in Example 1.

Formylheptenyl methoxymethyl ether (2: $R^3$=H; a=4)

Nuclear magnetic resonance spectrum: $^1$H-NMR (500 MHz, $CDCl_3$): δ=1.55-1.66 (4H, m), 2.35 (2H, ddt, J=1.6 Hz, 7.1 Hz, 7.1 Hz), 3.33 (3H, s), 3.52 (2H, t, J=6.1 Hz), 4.59 (2H, s), 6.10 (1H, ddt, J=15.7 Hz, 8.0 Hz, 1.6 Hz), 6.83 (1H, dt, J=15.7 Hz, 6.9 Hz), 9.48 (1H, d, J=8.0 Hz); $^{13}$C-NMR (500 MHz, $CDCl_3$): δ=24.52, 29.10, 32.33, 55.07, 67.09, 96.33, 133.06, 158.26, 193.95.

Mass spectrum: EI-mass spectrum (70 eV): m/z 127 ($M^+$-45), 114, 81, 68, 55, 45.

Infrared absorption spectrum (NaCl): ν=2938, 2882, 2822, 1692, 1149, 1111, 1043, 977, 918.

Comparative Example 6: Preparation of Formylheptenyl methoxymethyl ether (2: $R^3$=H; a=4), $CH_3OCH_2O(CH_2)_4CH$=$CHCHO$

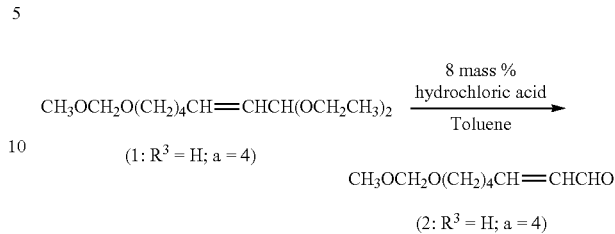

Diethoxyheptenyl methoxymethyl ether (1: $R^3$=H; a=4) (100.00 g, 0.39 mol, purity 95.97%) and toluene (24.70 g) were placed in a reactor at room temperature and stirred at 10 to 15° C. for 3 minutes. After the completion of stirring, 8 mass % hydrochloric acid (44.80 g, 0.098 mol of hydrogen chloride) was added dropwise at 15 to 20° C. to cause hydrolysis. The progress of hydrolysis was monitored by GC at 15 to 20° C. After a conversion was confirmed to be 99.5% or more, the reaction was stopped. The reaction time from the dropwise addition of 8 mass % hydrochloric acid to the termination of the reaction was 1 hour. Toluene (61.74 g) was further added to the reaction mixture, followed by phase separation. The aqueous phase was then removed to obtain the organic phase. Then, the resulting organic phase was washed with brine, followed by phase separation. The aqueous phase was then removed to obtain the organic phase. The resulting organic phase was further washed with an aqueous solution of sodium bicarbonate, followed by phase separation. The aqueous phase was then removed to obtain the organic phase. The resulting organic phase was subjected to distillation at a reduced pressure to obtain formylheptenyl methoxymethyl ether (2: $R^3$=$CH_3$; a=4) (61.03 g, 0.32 mol, purity 90.97%, b.p.=108.2 to 109.8° C./3.0 mmHg (0.40 kPa)) in a yield of 82.75%.

Various spectrum data of the formylheptenyl methoxymethyl ether (2: $R^3$=H; a=4) thus prepared were the same as those obtained in Example 4.

Example 5: Preparation of (5E,7Z)-5,7-dodecadienyl alkoxymethyl ether Compound (4: $R^3$=H; a=4), $CH_3(CH_2)_3CH$=$CHCH$=$CH(CH_2)_4OCH_2OCH_3$

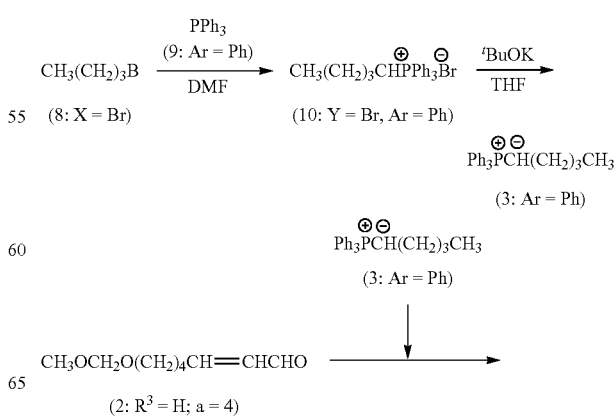

-continued

CH$_3$OCH$_2$O(CH$_2$)$_4$CH=CHCH=CH(CH$_2$)$_3$CH$_3$ (4: R$^3$ = H; a = 4)

1-Bromopentane (8: X=Br) (182.77 g, 1.21 mol), triphenylphosphine (9: each Ar=Ph) (315.50 g, 1.20 mol), and N,N-dimethylformamide (DMF) (200.00 g) were placed in a reactor at room temperature and stirred at 110 to 120° C. for 9 hours to prepare pentyltriphenylphosphonium bromide (10: Y=Br; each Ar=Ph). Next, tetrahydrofuran (872.84 g) was added dropwise to the reaction mixture at 30 to 40° C. After the completion of the dropwise addition, the reaction mixture was cooled to −5 to 10° C., and potassium t-butoxide (131.29 g, 1.17 mol) was added and stirred for 1 hour to prepare triphenylphosphonium pentylide (3: Ar=Ph).

Formylheptenyl methoxymethyl ether obtained in Example 4 (2: R$^3$=H; a=4) (185.72 g, 1.00 mol, purity 92.73%) was then added dropwise at −72 to −61° C. After the completion of the dropwise addition, the mixture was heated to room temperature and stirred at 25 to 30° C. for 1 hour. Water (592.67 g) was then added to the reaction mixture, followed by phase separation. The aqueous phase was then removed to obtain the organic phase. The resulting organic phase was subjected to distillation at a reduced pressure to obtain (5E,7Z)-5,7-dodecadienyl alkoxymethyl ether compound (4: R$^3$=H; a=4) (230.28 g, 0.97 mol, purity 95.82%; 5E7Z:5E7E:5Z7Z=91.8:6.6:1.6, b.p.=104.0 to 123.5° C./3.0 mmHg (0.40 kPa)) in a yield of 97.48%.

(5E,7Z)-5,7-Dodecadienyl alkoxymethyl ether Compound (4: R$^3$=H; a=4)

Nuclear magnetic resonance spectrum: $^1$H-NMR (500 MHz, CDCl$_3$): δ=0.90 (3H, t, J=7.3 Hz), 1.28-1.39 (4H, m), 1.42-1.51 (2H, quin-like, J=7.3 Hz), 1.57-1.64 (2H, quin-like, J=7.3 Hz), 2.10-2.18 (4H, m), 3.35 (3H, s), 3.52 (2H, t, J=6.5 Hz), 4.61 (2H, s), 5.30 (1H, dt, J=10.9 Hz, 7.6 Hz), 5.64 (1H, dt, J=14.5 Hz, 7.6 Hz), 5.93 (1H, dd, J=11.1 Hz, 11.1 Hz), 6.29 (1H, dddt, J=14.9 Hz, 11.1 Hz, 2.7 Hz, 1.2 Hz); $^{13}$C-NMR (500 MHz, CDCl$_3$): δ=13.92, 22.28, 25.96, 27.35, 29.22, 31.85, 32.55, 55.04, 67.54, 96.32, 125.95, 128.43, 130.27, 133.94.

Mass spectrum: EI-mass spectrum (70 eV): m/z 226 (M$^+$), 194, 181, 163, 150, 137, 121, 107, 95, 79, 67, 45.

Infrared absorption spectrum (NaCl): ν=2929, 2872, 1458, 1440, 1150, 1112, 1044, 983, 949, 921, 732.

Example 6: Preparation of (5E,7Z)-5,7-dodecadiene-1-ol (5), CH$_3$(CH$_2$)$_3$CH=CHCH=CH(CH$_2$)$_4$OH

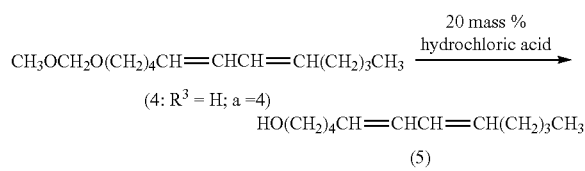

(5E,7Z)-5,7-Dodecadienyl alkoxymethyl ether compound obtained in Example 5 (4: R$^3$=H; a=4) (210.84 g, 0.89 mol, purity 95.82%; 5E7Z:5E7E:5Z7Z=91.8:6.6:1.6) and methanol (446.25 g, 13.93 mol) were placed in a reactor equipped with a distillation tower and stirred at 45 to 50° C., and 20 mass % hydrochloric acid (44.63 g, 0.24 mol of hydrogen chloride) was added dropwise to the mixture at 45 to 50° C.

Subsequently, the reaction mixture was heated to 60° C. and stirred for 3 hours. After the completion of stirring, the internal temperature was raised to 65 to 70° C., and a mixture of by-produced dimethoxymethane and by-produced methanol was distilled off and removed through the distillation tower. The reaction mixture was sampled during the reaction. After a conversion was confirmed to be 100%, the distillation was stopped. The reaction mixture was cooled to 35° C., and water (286 g) was added to the reaction mixture, followed by phase separation. The aqueous phase was then removed to obtain the organic phase. The resulting organic phase was subjected to distillation at a reduced pressure to obtain (5E,7Z)-5,7-dodecadien-1-ol (5) (162.54 g, 0.81 mol, purity 91.35%; 5E7Z:5E7E:5Z7Z=91.1:7.1:1.8, b.p.=106.2 to 115.6° C./3.0 mmHg (0.40 kPa)) in a yield of 91.26%.

(5E,7Z)-5,7-Dodecadiene-1-ol (5)

Nuclear magnetic resonance spectrum: $^1$H-NMR (500 MHz, CDCl$_3$): δ=0.89 (3H, t, J=7.3 Hz), 1.24-1.40 (4H, m), 1.46 (2H, quin-like, J=7.3 Hz), 1.58 (2H, quin-like, J=7.3 Hz), 1.72 (1H, br. s), 2.14 (4H, sext-like, J=6.5 Hz), 3.64 (2H, t, J=6.5 Hz), 5.30 (1H, dt, J=10.9 Hz, 7.6 Hz), 5.64 (1H, dt, J=14.6 Hz, 7.3 Hz), 5.93 (1H, dd, J=11.1 Hz, 11.1 Hz), 6.31 (1H, dddt, J=15.1 Hz, 11.0 Hz, 1.5 Hz, 1.5 Hz); $^{13}$C-NMR (500 MHz, CDCl$_3$): δ=13.92, 22.28, 25.45, 27.35, 31.84, 32.20, 32.50, 62.73, 125.97, 128.39, 130.33, 133.90.

Mass spectrum: EI-mass spectrum (70 eV): m/z 182 (M$^+$), 164, 149, 135, 121, 107, 93, 79, 67, 55, 41.

Infrared absorption spectrum (NaCl): ν=3338, 2956, 2930, 1457, 1059, 982, 949, 730.

Example 7: Preparation of (5E,7Z)-5,7-dodecadienyl acetate (6), CH$_3$(CH$_2$)$_3$CH=CHCH=CH(CH$_2$)$_4$OCOCH$_3$

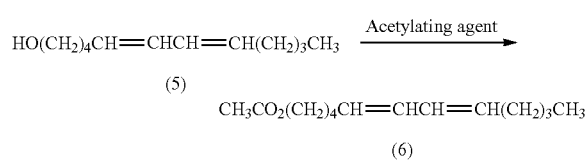

(5E,7Z)-5,7-Dodecadiene-1-ol (5) obtained in Example 6 (154.50 g, 0.77 mol, purity 91.35%; 5E7Z:5E7E:5Z7Z=91.1:7.1:1.8) and pyridine (97.98 g, 1.24 mol) were placed in a reactor at room temperature and stirred at 15 to 25° C. for 13 minutes. After the completion of stirring, acetic anhydride (94.85 g, 0.93 mol) was added dropwise at 20 to 40° C. and stirred at 30 to 35° C. for 6 hours. Next, water (203.36 g) was added to the reaction mixture, followed by phase separation. The aqueous phase was then removed to obtain the organic phase. The resulting organic phase was subjected to distillation at a reduced pressure to obtain (5E,7Z)-5,7-dodecadienyl acetate (6) (181.52 g, 0.76 mol, purity 93.93%; 5E7Z:5E7E:5Z7Z=91.5:6.8:1.7, b.p.=120.0 to 123.0° C./4.0 mmHg (0.53 kPa)) in a yield of 98.17%.

(5E,7Z)-5,7-Dodecadienyl acetate (6)

Nuclear magnetic resonance spectrum: $^1$H-NMR (500 MHz, CDCl$_3$): δ=0.89 (3H, t, J=7.3 Hz), 1.27-1.40 (4H, m), 1.45 (2H, quin-like, J=7.6 Hz), 1.63 (2H, quin-like, J=6.9 Hz), 2.03 (3H, s), 2.14 (4H, sext-like, J=6.9 Hz), 4.05 (2H, t, J=6.5 Hz), 5.31 (1H, dt, J=10.7 Hz, 7.6 Hz), 5.62 (1H, dt, J=14.5 Hz, 6.9 Hz), 5.93 (1H, dd, J=11.1 Hz, 11.1 Hz), 6.30 (1H, ddd, J=15.3 Hz, 11.1 Hz, 1.2 Hz); $^{13}$C-NMR (500 MHz, CDCl$_3$): δ=13.91, 20.94, 22.27, 25.65, 27.35, 28.07, 31.83, 32.33, 64.34, 126.15, 128.34, 130.45, 133.53, 171.13.

Mass spectrum: EI-mass spectrum (70 eV): m/z 224 (M$^+$), 181, 164, 149, 136, 121, 107, 93, 79, 67, 55.

Infrared absorption spectrum (NaCl): ν=2956, 2930, 2859, 1742, 1457, 1365, 1238, 1039, 984, 950, 733.

The invention claimed is:

1. A process for preparing a formylalkenyl alkoxymethyl ether compound of the following general formula (2):

R$^3$CH$_2$OCH$_2$O(CH$_2$)$_a$CH=CHCHO  (2)

wherein R$^3$ represents a hydrogen atom, an n-alkyl group having 1 to 9 carbon atoms, or a phenyl group, and "a" represents an integer of 1 to 10,
the process comprising:
hydrolyzing a dialkoxyalkenyl alkoxymethyl ether compound of the following general formula (1):

R$^3$CH$_2$OCH$_2$O(CH$_2$)$_a$CH=CHCH(OR$^1$)(OR$^2$)  (1)

wherein R$^1$ and R$^2$ represent, independently of each other, a monovalent hydrocarbon group having 1 to 15 carbon atoms, or R$^1$ and R$^2$ may form together a divalent hydrocarbon group, R$^1$-R$^2$, having 2 to 10 carbon atoms; and R$^3$ and "a" are as defined above,
in the presence of an acid, while removing an alcohol compound thus generated to form the formylalkenyl alkoxymethyl ether compound (2).

2. The process for preparing the formylalkenyl alkoxymethyl ether compound (2) according to claim 1, wherein the acid is formic acid, hydrochloric acid or a combination thereof.

3. A process for preparing a (5E,7Z)-5,7-dodecadien-1-ol of the following formula (5):

CH$_3$(CH$_2$)$_3$CH=CHCH=CH(CH$_2$)$_4$OH  (5)

the process comprising
the process for preparing the formylalkenyl alkoxymethyl ether compound (2) according to claim 1, provided that "a" is 4,
subjecting the formylalkenyl alkoxymethyl ether compound (2) thus obtained, and a triarylphosphonium pentylide compound of the following general formula (3):

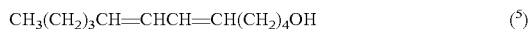

Ar$_3$$\overset{\oplus}{P}$$\overset{\ominus}{C}$H(CH$_2$)$_3$CH$_3$  (3)

wherein Ar represents, independently of each other, an aryl group,
to a Wittig reaction to form a (5E,7Z)-5,7-dodecadienyl alkoxymethyl ether compound of the following general formula (4):

CH$_3$(CH$_2$)$_3$CH=CHCH=CH(CH$_2$)$_4$OCH$_2$OCH$_2$R$^3$  (4)

wherein R$^3$ is as defined above; and
subjecting the (5E,7Z)-5,7-dodecadienyl alkoxymethyl ether compound (4) to dealkoxymethylation to form the (5E,7Z)-5,7-dodecadiene-1-ol (5).

4. A process for preparing a (5E,7Z)-5,7-dodecadienyl acetate of the following formula (6):

CH$_3$(CH$_2$)$_3$CH=CHCH=CH(CH$_2$)$_4$OCOCH$_3$  (6)

the process comprising
the process for preparing the (5E,7Z)-5,7-dodecadiene-1-ol (5) according to claim 3, and
subjecting the (5E,7Z)-5,7-dodecadiene-1-ol (5) thus obtained to an acetylation to form the (5E,7Z)-5,7-dodecadienyl acetate (6).

5. A process for preparing a (5E,7Z)-5,7-dodecadiene-1-ol of the following formula (5):

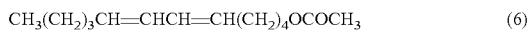

CH$_3$(CH$_2$)$_3$CH=CHCH=CH(CH$_2$)$_4$OH  (5)

the process comprising
the process for preparing the formylalkenyl alkoxymethyl ether compound (2) according to claim 2, provided that "a" is 4,
subjecting the formylalkenyl alkoxymethyl ether compound (2) thus obtained, and a triarylphosphonium pentylide compound of the following general formula (3):

Ar$_3$$\overset{\oplus}{P}$$\overset{\ominus}{C}$H(CH$_2$)$_3$CH$_3$  (3)

wherein Ar represents, independently of each other, an aryl group, to a Wittig reaction to form a (5E,7Z)-5,7-dodecadienyl alkoxymethyl ether compound of the following general formula (4):

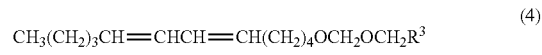

CH$_3$(CH$_2$)$_3$CH=CHCH=CH(CH$_2$)$_4$OCH$_2$OCH$_2$R$^3$  (4)

wherein R$^3$ is as defined above; and
subjecting the (5E,7Z)-5,7-dodecadienyl alkoxymethyl ether compound (4) to dealkoxymethylation to form the (5E,7Z)-5,7-dodecadiene-1-ol (5).

6. A process for preparing a (5E,7Z)-5,7-dodecadienyl acetate of the following formula (6):

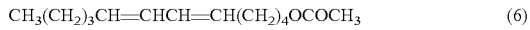

CH$_3$(CH$_2$)$_3$CH=CHCH=CH(CH$_2$)$_4$OCOCH$_3$  (6)

the process comprising
the process for preparing the (5E,7Z)-5,7-dodecadiene-1-ol (5) according to claim 5, and
subjecting the (5E,7Z)-5,7-dodecadiene-1-ol (5) thus obtained to an acetylation to form the (5E,7Z)-5,7-dodecadienyl acetate (6).

* * * * *